(12) United States Patent
Martin et al.

(10) Patent No.: US 8,796,277 B2
(45) Date of Patent: Aug. 5, 2014

(54) RADIOPROTECTOR COMPOUNDS AND RELATED METHODS

(75) Inventors: Roger Francis Martin, Ivanhoe (AU); Jonathan Michael White, Wheelers Hill (AU)

(73) Assignee: Peter MacCallum Cancer Institute, East Melbourne (AU)

( * ) Notice: Subject to any disclaimer, the term of this patent is extended or adjusted under 35 U.S.C. 154(b) by 135 days.

(21) Appl. No.: 12/520,356

(22) PCT Filed: Dec. 21, 2007

(86) PCT No.: PCT/AU2007/001990
§ 371 (c)(1),
(2), (4) Date: Aug. 7, 2009

(87) PCT Pub. No.: WO2008/074091
PCT Pub. Date: Jun. 26, 2008

(65) Prior Publication Data
US 2010/0022557 A1    Jan. 28, 2010

(30) Foreign Application Priority Data
Dec. 21, 2006  (AU) .................................. 2006907254

(51) Int. Cl.
*A61K 31/496* (2006.01)
*C07D 235/20* (2006.01)

(52) U.S. Cl.
USPC ...................................... 514/254.06; 544/370

(58) Field of Classification Search
None
See application file for complete search history.

(56) References Cited

U.S. PATENT DOCUMENTS 3,538,097 A    11/1970   Loewe et al.

FOREIGN PATENT DOCUMENTS

WO           97/04776 A1    2/1997

OTHER PUBLICATIONS

Burger's Medicinal Chemistry,edited by Manfred E. Wolff, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*
Vippagunta et al Advanced Drug Delivery Reviews, vol. 48, pp. 3-26 (2001).*
Mettler et al. AJR, vol. 196, pp. 616-618 (2011).*
Dumont et al. Expert Opin.Ther.Patents vol. 20, p. 73-101 (2010).*
Cary et al. Radiation Research vol. 177(5), pp. 663-675 (2012).*
Latt, Samuel A. et al: Spectral studies on 3328 Hoechst and related bisbenzimidazole useful for fluorescent detection of deoxyribonucleic acid synthesis; Journal of Histochemistry and Cytochemistry, vol. 24, No. 1, pp. 22-33, 1976.
Kelly, D. P. et al.: DNA Binding Copounds. VI Synthesis and Characterization of 2,5-Disubstituted Bibenzimidazoles Related to the DNA Minor Groove Binder Hoechst 33258; Australian Journal of Chemistry, CSIRO, AU, vol. 47, No. 9, Jan. 1, 1994, pp. 1751-1769.
Arzneimittel-Forschung, 1974, vol. 24 (12), p. 1927-1933.
English translation of Japanese Office Action for corresponding Japanese Application No. 2009-541697 mailing date: Jan. 4, 2013.

* cited by examiner

*Primary Examiner* — Emily Bernhardt
(74) *Attorney, Agent, or Firm* — Sughrue Mion, PLLC

(57) ABSTRACT

The invention relates to radioprotectors of formula (I), processes for their preparation and their use in protecting biological materials from radiation damage. In diagnostic and therapeutic radiology, particularly in cancer radiotherapy, the radioprotectors of the present invention may be used to protect certain normal tissues or structures from radiation damage. The radioprotectors of formula (I) may also have uses in decreasing the effects of irradiation in non-medical scenarios, both civil and military.

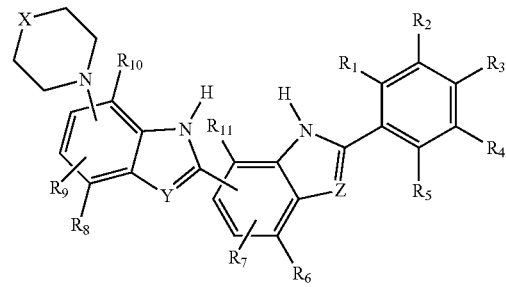

Formula (I)

9 Claims, 2 Drawing Sheets

RADIOPROTECTOR COMPOUNDS AND RELATED METHODS

FIELD OF THE INVENTION

The invention relates to radioprotectors, processes for their preparation and their use in protecting biological materials from radiation damage. In diagnostic and therapeutic radiology, particularly in cancer radiotherapy, radioprotectors may be used to protect certain normal tissues or structures from radiation damage. Radioprotectors also have uses in decreasing the effects of irradiation in non-medical scenarios, both civil and military. The invention relates in particular to radioprotector compounds substituted with fluorine and/or chlorine and, relative to known radioprotector compounds, that exhibit reduced cytotoxicity activity.

BACKGROUND OF THE INVENTION

It is generally accepted that DNA is the crucial target in the cytotoxic effects of ionising radiation. There is considerable evidence to support the view that DNA double-stranded (ds) breaks are particularly important. The DNA damage results from both direct ionisation in the DNA molecule (direct effect) and by indirect effects mediated by the radiolysis products of water. Carbon-centred radicals on the deoxyribose moiety of DNA are thought to be important precursors of strand breaks. Ionising radiation also induces damage in DNA bases. If the level of cellular DNA damage is sufficient, the consequence of irradiation is cell kill, and thus ionising radiation is used as a mode of cancer therapy. For irradiated normal tissues, the cell killing can result in temporary or permanent impairment of tissue and organ function. The extent of such effects is dependant upon the radiation dose, and if sufficient can be lethal to the organism. For humans and other animals, hematopoiesis is the most radiosensitive organ/function, followed by the gastrointestinal mucosa. Finally, even if the radiation induced DNA damage is sublethal, mutagenic lesions can have serious long term consequences, including carcinogenesis.

The medical strategies or countermeasures aimed at reducing the extent of the above radiation-induced effects are broadly described as radioprotectors (which to be effective, generally need to be administered prior to radiation exposure), mitigants/mitigators (which can be effective if administered after irradiation, but before the appearance of symptoms), and treatments which are generally administered after the appearance of symptoms. A sub-class of the prophylactic radioprotectors are drugs that reduce the extent of the initial radiation-induced DNA damage, and it is this sub-class that is the major focus of the present invention.

The commercial potential of radioprotectors resides primarily in two distinct arenas. One of these relates to the need to protect normal tissues in cancer radiotherapy patients, and the other concerns the need to assuage the consequences of unplanned irradiation associated with civil scenarios, such as radiation accidents and radiation terrorism, as well as irradiation in military contexts.

The treatment of tumours with ionising radiation (hereinafter referred to as "cancer radiotherapy") is used extensively in cancer therapy. The goal of such treatment is the destruction of tumour cells and inhibition of tumour cell growth presumably through DNA damage, while minimising damage to non-tumour cells and tissues. The potential for damage to non-tumour cells in the vicinity of the tumour limits the radiation dose that can be administered, which in turn often limits the effectiveness of radiotherapy against certain tumours. This is especially the case in relation to brain tumours and tumours in the abdominal cavity.

Cancer radiotherapy is a very significant public health activity. Given the incidence of cancer in the population and the international assessment that more than 50% of cancer patients benefit from inclusion of radiotherapy in their treatment, more than 10% of the population are likely to experience cancer radiotherapy in their lifetime.

The dominant consideration in prescribing radiation doses for cancer radiotherapy is the assessment of tolerance of the most radiosensitive normal tissues/organs in the treatment field. This assessment, together with the expected radiation dose required to eradicate a tumour, often determines whether the treatment strategy is aimed at cure or palliation. In many cases, the maximum tolerable doses are insufficient to eradicate the tumour. This dilemma is embodied in the concept of therapeutic ratio, which represents the ratio of probabilities of tumour control versus normal tissue morbidity. Approaches to improving the therapeutic ratio include:

(a) optimising the physical targeting of the radiation to the tumour;
(b) fractionation of the radiation dose; and
(c) the use of radiomodifiers.

Improving the physical delivery of radiation has had a considerable impact on the practice of radiotherapy. For example, increasing the energy of x-ray photons from several hundred kilovolts to the present-day megavoltage beams enables the zone of maximum radiation dose to be set at depths of several centimeters, whereas with the older machines the maximum dose was near the skin surface. There are a number of more sophisticated approaches to "tailoring" treatment beams in various stages of development and implementation. Brachytherapy, the use of implanted radioactive sources rather than external beams, is a further approach to improving the physical dose distribution.

Almost without exception, curative external beam radiotherapy involves fractionation of the radiation dose. An example of a conventional schedule would be a total of 60 Grays given in thirty 2 Gray fractions. Since cells have the capacity to repair radiation damage between fractions, the fractionated treatment results in much less cell-kill than a single dose of 60 Gray. However, normal cells generally have a greater repair capacity than do tumour cells, so the "sparing" effect of fractionation is more marked for normal tissues. In short, fractionation improves the therapeutic ratio.

Exploration of radiomodifiers such as radioprotectors and radiosensitisers has focused on hypoxic cell sensitisers such as metranidazole and misonidazole. Radioprotectors have received much less attention than radiosensitisers at the clinical level. The nuclear era spawned considerable effort in the development of radioprotectors with more than 4000 compounds being synthesised and tested at the Walter Reed Army Institute of Research in the United States of America in the 1960's. With the exception of a compound that was called WR2728 (later called Ethyol and now known as Amifostine) none of the compounds have proved useful for cancer radiotherapy, and even WR2728 was considered too toxic for administration in either the military or industrial contexts (i.e., protection against total body irradiation).

It is important to note the interplay between the three approaches (a)-(c), above, to improving the therapeutic ratio. A combination of improved physical targeting, fractionation and radiomodifiers could transform the intent in some radiotherapy situations from palliative to curative. For curative schedules, successful application of radiomodifiers would relax the requirement for fractionation and hence reduce overall costs of treatment, which to a large extent is proportional to the number of treatment fractions per patient.

A particularly important role for radioprotectors has emerged from the recognition that accelerated repopulation of tumour cells during radiotherapy can seriously compromise the effectiveness of treatment. The main consequences of this have been as follows:

(i) The development of accelerated treatment schedules to reduce the overall time of radiotherapy treatment. In such accelerated schedules, acute reactions are a particular problem. For example, acute oral mucositis in head and neck cancer patients indicates a clear need for radioprotectors.

(ii) The recognition that the interruption of radiotherapy treatment due to normal tissue reactions will reduce the probability of tumour control. Accordingly, the use of radioprotectors to prevent toxicity-induced treatment interruption would be clearly beneficial.

The events of 11 Sep. 2001 prompted assessments of vulnerability to many types of terrorism scenarios, amongst which is a collection described as radiological terrorism. An example is the so-called "dirty bomb" involving dispersal of some form a radioactivity with conventional explosive. Whilst attention is focused on the acute radiation syndrome (ARS; also referred to as "radiation sickness"), which describes the consequences of whole-body exposure to radiation doses greater than 1 Gy, there are also concerns about the longer-term effects of low doses, namely radiation-induced mutagenesis and carcinogenesis (1). This general situation, and the realisation that no prophylactic agents are available to provide protection against exposure to ionising radiation has generated significant research and political activity.

The mean lethal dose of radiation required to kill 50% of humans 60 days after whole-body irradiation ($LD_{50/60}$) is between 3.25 and 4 Gy without supportive care, and 6-7 Gy when antibiotics and transfusion support are provided (1). The mortality is largely attributed to the haematopoietic syndrome, a consequence of hypoplasia or aplasia of the bone marrow. Cytopenias develop as a result of radiation-induced and normal attrition of mature functional cells, combined with the failure of replacement because of radiation-induced depletion of haematopoietic stem cells and progenitors. The time and extent of cytopenia generally correlate with radiation dose and prognosis, but the kinetics of depletion and recovery of blood cells also varies between the erythropoiesis, myelopoiesis and thrombopoiesis lineages, thrombopoiesis being the slowest.

The gastrointestinal syndrome results from ablation of stem cells in intestinal crypts, which in turn leads to denudation of the intestinal mucosa. This injury occurs after whole-body doses in the range of 3-15 Gy and in rodents doses at the upper end of this range usually result in death within about 1 week after irradiation.

Countermeasures against unplanned irradiation include a wide range of potential molecular and cellular interventions. However, the mechanistic simplicity of chemical radioprotection—that is, reduction of radiation-induced DNA damage—is attractive because of its widespread potential. In this context, the possible need for protection of individuals at risk of exposure to low radiation doses, to thereby minimise long-term radiation effects such as mutagenesis and carcinogenesis, is particularly important. Such individuals would include emergency personnel involved in response to unplanned exposures, as well as those subject to occupational exposure to ionising radiation.

A further group would be patients exposed to ionizing radiation during diagnostic medical procedures conducted in diagnostic radiology and nuclear medicine departments of hospitals and outpatient facilities.

The radioprotective properties of the minor groove binding DNA ligand Hoechst 33342 were first described by Smith, P. J. and Anderson, C. O. (2), who used clonogenic survival assays of irradiated cultured cells. Young, S. D. and Hill, R. P. (3) reported similar effects in cultured cells, but extended their studies to in vivo experiments. They concluded that the lack of radioprotection in their in vivo experiments was due to insufficient levels of Hoechst 33342 being delivered to target cells following intravenous injection. The findings of Hill and Young underline an important requirement for effective radioprotectors, namely potency. If the radioprotector is more potent, then it is more likely to achieve the required concentrations in an in vivo setting.

There is another aspect to be considered apart from potency. The concentration required for radioprotection must be non-toxic regardless of the potency of the radioprotector. If the radioprotector is delivered systemically, then this lack of toxicity requirement includes not just the cells and tissues to be protected from the radiation, but extends to the toxicity to the subject as a whole. In the case of Hoechst 33342 toxicity limits the extent to which it is useful as a radioprotector.

There is also a substantial conceptual problem in using radioprotectors in cancer radiotherapy. In attempting to decrease the effect of radiation on normal tissues by application of radioprotectors, there is a fear that some of the radioprotector will reach the tumour, thereby compromising tumour cell kill. The existing radioprotectors, e.g. WR2727, are relatively small, diffusible molecules which do not avidly bind to tissue components and can therefore penetrate effectively through cell layers, so that they can reach the tumour via the circulation.

There is a need for radioprotectors that have limited penetration through cell layers. Such a property enables radioprotectors to be applied locally or topically to critical radiosensitive normal tissues in the vicinity of the tumour. Limited penetration restricts the extent to which the radioprotector reaches the capillary bed and is taken up into the circulation thereby reaching the tumour by systemic delivery in sufficient concentrations to confer significant radioprotection to the tumour.

The limited diffusion of DNA-binding ligands such as Hoechst 33342 through cell layers is known and has been exploited in mapping the location of cells in multi-cellular spheroids and in vivo, with respect to perfusion. Thus perfusion of Hoechst 33342 is considered a surrogate marker for perfusion of oxygen. In addition to restricting access to the tumour by systemic uptake following local or topical application to normal tissues, there is a further potential advantage of limited penetration in the context of cancer radiotherapy. This advantage stems from the view that the vasculature, in particular the endothelial cells, are the critical targets that determine the damaging effects of radiation. Furthermore, most radioresistant cells in the tumour are those viable cells that are most distant from the capillaries. The radioresistance of these cells is due to their hypoxic state, which in turn reflects their remoteness from the capillaries.

Consequently, radioprotectors having limited diffusion, when administered intravenously, will be delivered more efficiently to critical radiosensitive cells in animal tissues, than to the subpopulation of cells in tumours (ie. hypoxic cells) which limit the effectiveness of radiotherapy generally. Thus, the use of such radioprotectors would be expected to enable higher radiation doses to be used, with increased probability of killing the hypoxic cells in the tumour.

However, the potential of the combination of these radiobiological features and the characteristics of DNA-binding radioprotectors can only be useful in cancer radiotherapy provided that an over-riding and necessary requirement of the radioprotectors exists, namely that the radioprotectors are sufficiently potent as to confer demonstrable radioprotection at non-toxic concentrations, when applied topically or systemically. A further practical requirement is that the extent of the limited penetration is sufficient to prevent significant systemic uptake following topical application, but not so pronounced so as to prevent sufficient concentrations from reaching the cells that determine the radiosensitivity of the tissue to be protected from the effects of ionising radiation, by topical or local application.

The extent of radioprotection (in the contexts of both cancer radiotherapy and protection from unplanned radiation exposure) is generally described in terms of dose modification factor (DMF), which is defined as the ratio of radiation doses required to produce the equivalent radiation-induced effect (molecular, cellular or in vivo endpoint) in the presence and absence of the radioprotector. When the radioprotective effect is observed on the basis of an in vivo endpoint, mechanisms other than modification of the initial radiation-induced damage may be involved. For example, for both the haematopoietic syndrome and the gastrointestinal syndrome, infection plays an important role in ultimate mortality, as a consequence of neutropenia and breach of the intestinal mucosal barrier, respectively. Thus, some immunostimulants have potential as mitigators of the radiation response. Immunostimulants can also be effective post-irradiation.

International patent publication No. WO97/04776 and the subsequent publication by Martin et al (4) disclose certain bibenzimidazole compounds characterised by substitution with sterically hindering and electron donating groups. Although these compounds demonstrate strong radioprotective activity there is scope to reduce the inherent cytotoxicity of compounds of this general class. The challenge, however, is to do so while retaining, and preferably improving, radioprotective activity (measured as dose modification factor). The disclosures of WO97/04776 are included herein in their entirety by way of reference.

A requirement accordingly exists for radioprotectors that can be used in cancer radiotherapy, in protection of biological material from effects of radiation exposure and/or in protection of humans or animals from the effects of unplanned irradiation, which demonstrate reduced cytotoxicity but that retain radioprotective potency, and preferably that penetrate through cell layers to a limited extent. In particular it is desirable that such compounds may be administered topically to protect tissues such as the skin, oral mucosa, oesophageal mucosa, rectal mucosa, vaginal mucosa and bladder epithelium, as well as parenterally to protect organs such as the lung and brain.

SUMMARY OF THE INVENTION

According to one embodiment of the present invention there is provided a radioprotector compound of formula (I)

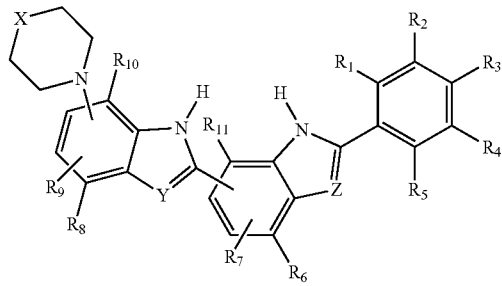

Formula (I)

wherein:

X is optionally substituted alkylamino or optionally substituted alkyl;

Y and Z are the same or different and are selected from N and C(R') wherein R' is hydrogen, optionally substituted alkyl or optionally substituted alkenyl;

and $R_1$ to $R_{11}$ may be the same or different and are selected from fluorine, chlorine, hydrogen and an electron donating group, or any two of $R_1$ to $R_{11}$ and NH may together with the carbon atoms to which they are attached form an optionally substituted ring which may contain heteroatoms, provided that at least one of $R_1$ to $R_{11}$ is fluorine or chlorine;

and salts, pharmaceutically acceptable derivatives, prodrugs and/or tautomers thereof.

Preferably at least one other of $R_1$ to $R_{11}$ is an electron donating group.

According to another embodiment of the present invention there is provided a radioprotector compound which is selected from:

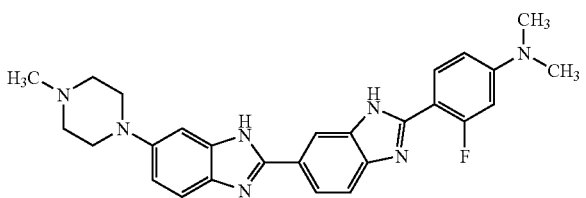

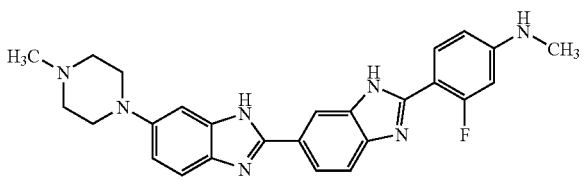

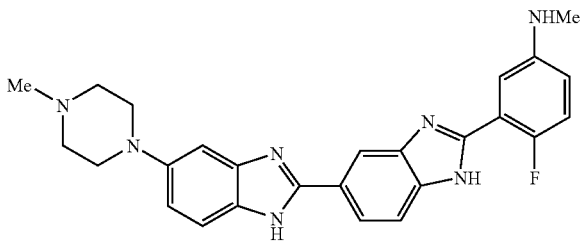

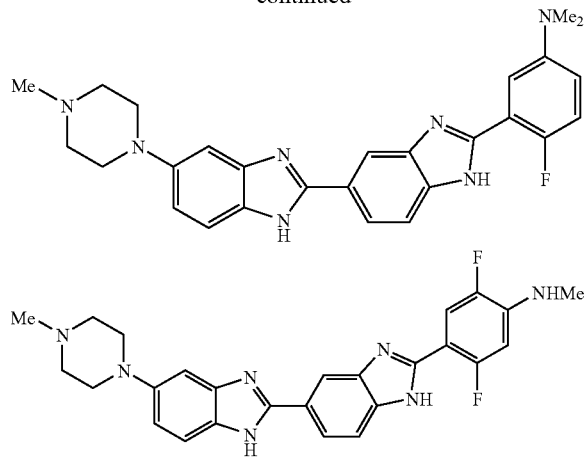

In a still further embodiment of the invention there is provided a method for protecting a subject from radiation damage, or reducing radiation damage in a subject, which comprises administering to the subject an effective amount of a radioprotector compound as mentioned above, before exposure or continuing exposure of the subject to radiation.

In a further embodiment of the invention there is provided a method of cancer radiotherapy which comprises preferentially administering to non-tumour cells and tissues in a subject in need of such therapy an amount of a radioprotector compound as mentioned above effective to minimise damage to the non-tumour cells and tissues, and subjecting the locus of a tumour in the subject to radiation.

In a further embodiment of the invention there is provided a method of protecting biological material from radiation damage, or reducing radiation damage in biological material, which comprises exposing the biological material to a radioprotector compound as mentioned above for a time sufficient to allow association of the compound with DNA in the biological material, before exposure or continuing exposure of the material to radiation.

In another embodiment of the invention there is provided use of a radioprotector compound as mentioned above as a radioprotector.

In a further embodiment of the invention there is provided use of a radioprotector compound as mentioned above in preparation of a medicament for use as a radioprotector.

In a further embodiment of the invention there is provided use of a radioprotector compound as mentioned above in preparation of a medicament for use as a radioprotector in conjunction with cancer radiotherapy.

In a further embodiment of the invention there is provided a pharmaceutical composition comprising a radioprotector compound as mentioned above and one or more pharmaceutically acceptable carriers and/or diluents.

BRIEF DESCRIPTION OF THE FIGURES

In the Examples, reference will be made to the accompanying drawings in which.

DETAILED DESCRIPTION OF THE INVENTION

Figure 1:
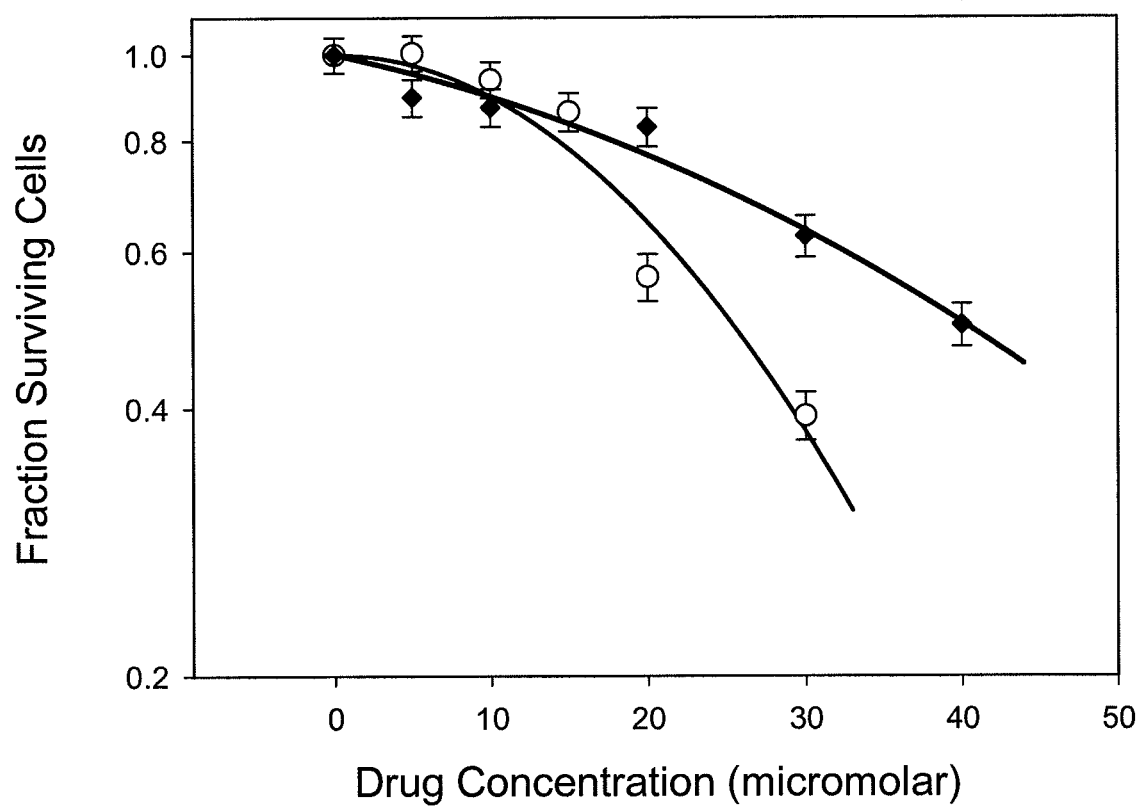
FIG. 1 shows a plot of clonogenic survival of un-irradiated cells after incubation with increasing radioprotector concentrations (μM). The data for methylproamine (Formula I; X=MeN, Y=N, Z=N, $R_1$=Me, $R_3$=$NMe_2$) is represented by open circles. The filled diamonds show the data for the compound of Example 1 (orthoFluoroProamine) (Formula I; X=MeN, Y=N, Z=N, $R_1$=F, $R_3$=$NMe_2$).

Throughout this specification, unless the context requires otherwise, the word "comprise", or variations such as "comprises" or "comprising", will be understood to imply the inclusion of a stated integer or group of integers but not the exclusion of any other integer or group of integers.

The reference to any prior art in this specification is not, and should not be taken as, an acknowledgment or any form of suggestion that that prior art forms part of the common general knowledge in Australia.

The term "electron donating group" is used herein in its broadest sense and generally encompasses those substituents having a negative Hammett substituent constant σ, as defined by the Hammett equation. The Hammett equation is as follows:

$$\text{Log } k/k_o = \sigma\rho$$

where k is the equilibrium or rate constant for the substituted compound, $k_o$ is the equilibrium or rate constant for the unsubstituted compound and ρ is a constant, the value of which depends on reaction type and conditions (e.g. solvent). Most usually Hammett substituent constants are derived from ionisation constants of substituted benzoic acids relative to that of unsubstituted benzoic acid, and extensive compilations have been reported (see for example C. Hansch, A. Ieo and R. W. Taft, *Chemical Reviews* 91, 165-195, 1991, the disclosure of which is included herein in its entirety by way of reference).

Electron donating groups include, but are not limited to, optionally substituted alkyl, optionally substituted alkenyl, NHR', $NR'_2$, OR' and SR', wherein R' is hydrogen, optionally substituted alkyl or optionally substituted alkenyl. Preferably the electron donating group is NHR' or $NR'_2$. It is postulated that the presence of at least one electron donating group increases radioprotective activity of the compound in question.

While not wishing to be limited by theory it is believed that the protection conferred by the compounds according to the invention is achieved by electron donation (reduction) by the radioprotector of transient radiation induced oxidizing species on the DNA. Since the radioprotectors may contain basic groups, protonation of these groups at physiological pH would be expected to substantially diminish this electron donating ability. The inventors have further speculated that inclusion of electron withdrawing groups such as fluorine and chlorine may reduce the basicity of the benzimidazole moiety, to thereby reduce cytotoxicity, but without significant loss of radioprotective activity.

General examples of compounds of formula (I) that include optionally substituted rings are provided below as general structures A to J. Apart from decreasing the unfavourable entropy change upon DNA-binding, the saturated rings are believed to prevent co-planarity of adjacent rings and hence intermolecular stacking and consequent aggregation.

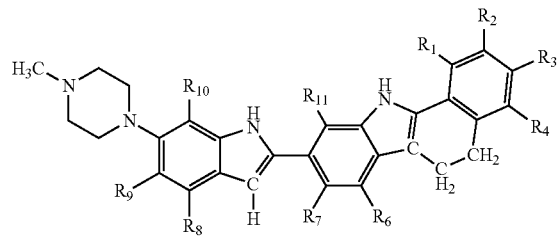

A

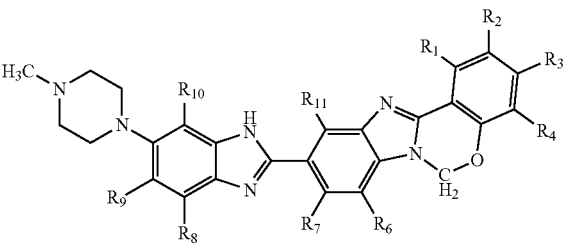

G

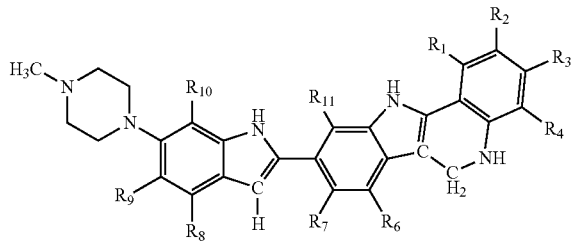

B

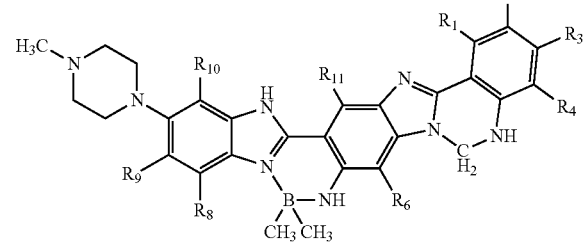

H

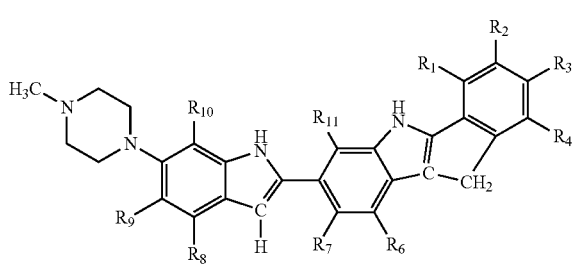

C

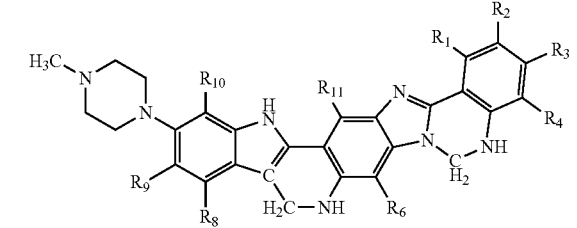

I

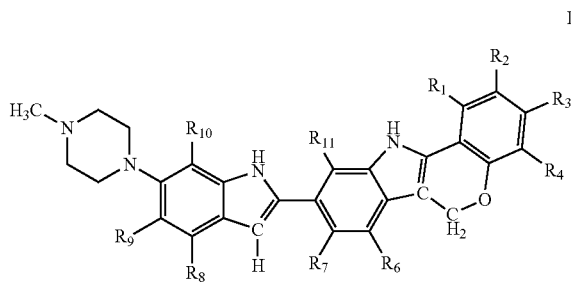

D

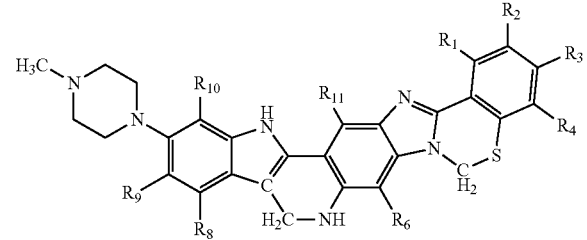

J

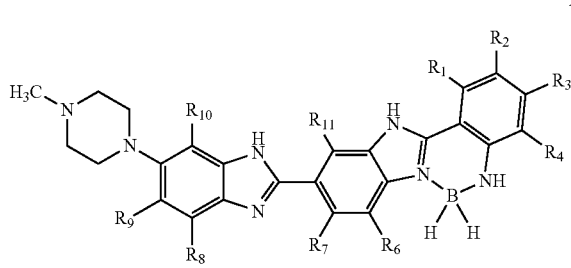

E

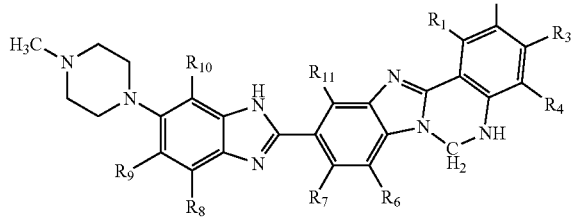

F wherein $R_1$ to $R_4$ and $R_6$ to $R_{11}$ are the same or different and are selected from hydrogen, fluorine, chlorine and an electron donating group and where at least one of $R_1$ to $R_4$ and $R_6$ to $R_{11}$ is F or Cl. Preferably at least one other of $R_1$ to $R_4$ and $R_6$ to $R_{11}$ is an electron donating group.

The term "alkyl" used either alone or in phrases such as "optionally substituted alkyl", "optionally substituted alkylamino" or "optionally substituted alkylene" is intended to encompass straight chain, branched or mono- or poly-cyclic alkyl, which is preferably $C_1$ to $C_{30}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like.

The term "alkenyl" used either alone or in compound words such as "optionally substituted alkenyl" denotes groups formed from straight chain, branched or mono- or poly-cyclic alkenes including ethylenically mono- or poly-unsaturated alkyl or cycloalkyl groups as defined above, preferably $C_{2-30}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "optionally substituted ring which may contain heteroatoms" is used herein in its broadest sense to refer to a saturated or unsaturated, homogenous or heterogeneous cyclic groups, such as, cycloalkyl, cycloalkenyl, cycloalkynyl, aryl or heterocyclyl which may contain heteroatoms selected from oxygen, nitrogen and sulphur. Examples of cycloalkyl and cycloalkenyl are described above. Suitable aryl includes single, polynuclear, conjugated and fused residues of aromatic hydrocarbons, such as, phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like. Examples of heterocyclyl include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydo, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

The salts of the compound of formula (I) are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids.

By "pharmaceutically acceptable derivative" is meant any pharmaceutically acceptable salt, hydrate, solvate or any other compound which, upon administration to the subject, is capable of providing (directly or indirectly) a compound of formula (I) or an active metabolite or residue thereof.

The term "pro-drug" is used herein in its broadest sense to include those compounds which are converted in vivo to compounds of formula (I).

The term "tautomer" is used herein in its broadest sense to include compounds of formula (I) which are capable of existing in a state of equilibrium between two isomeric forms. Such compounds may differ in the bond connecting two atoms or groups and the position of these atoms or groups in the compound. This term in particular encompasses keto-enol tautomers.

The compounds of the invention may be electrically neutral or be in the form of polycations with associated anions for electrical neutrality. Suitable associated anions include sulphate, tartrate, citrate, chloride, nitrate, nitrite, phosphate, perchlorate, halosulfonate or trihalomethylsulfonate.

Preferred compounds of formula (I) are those wherein X is alkylamino, Y and Z are N and wherein one or both of $R_2$ and $R_3$ are an electron donating group, with at least one of $R_1$ to $R_5$ (if not an electron donating group) being F or Cl. Most preferably at least one of $R_1$ to $R_5$ is F.

Particularly preferred electron donating groups include —$N(CH_3)_2$, —$NH(CH_3)$, —$OCH_3$ and —$OCH_2CH_3$.

In a further particularly preferred embodiment of the invention $R^1$ and/or $R_5$ is F or Cl (preferably F) when $R_2$ or $R_3$ is an electron donating group.

Structures of some preferred compounds according to the invention are provided below as structures K to W:

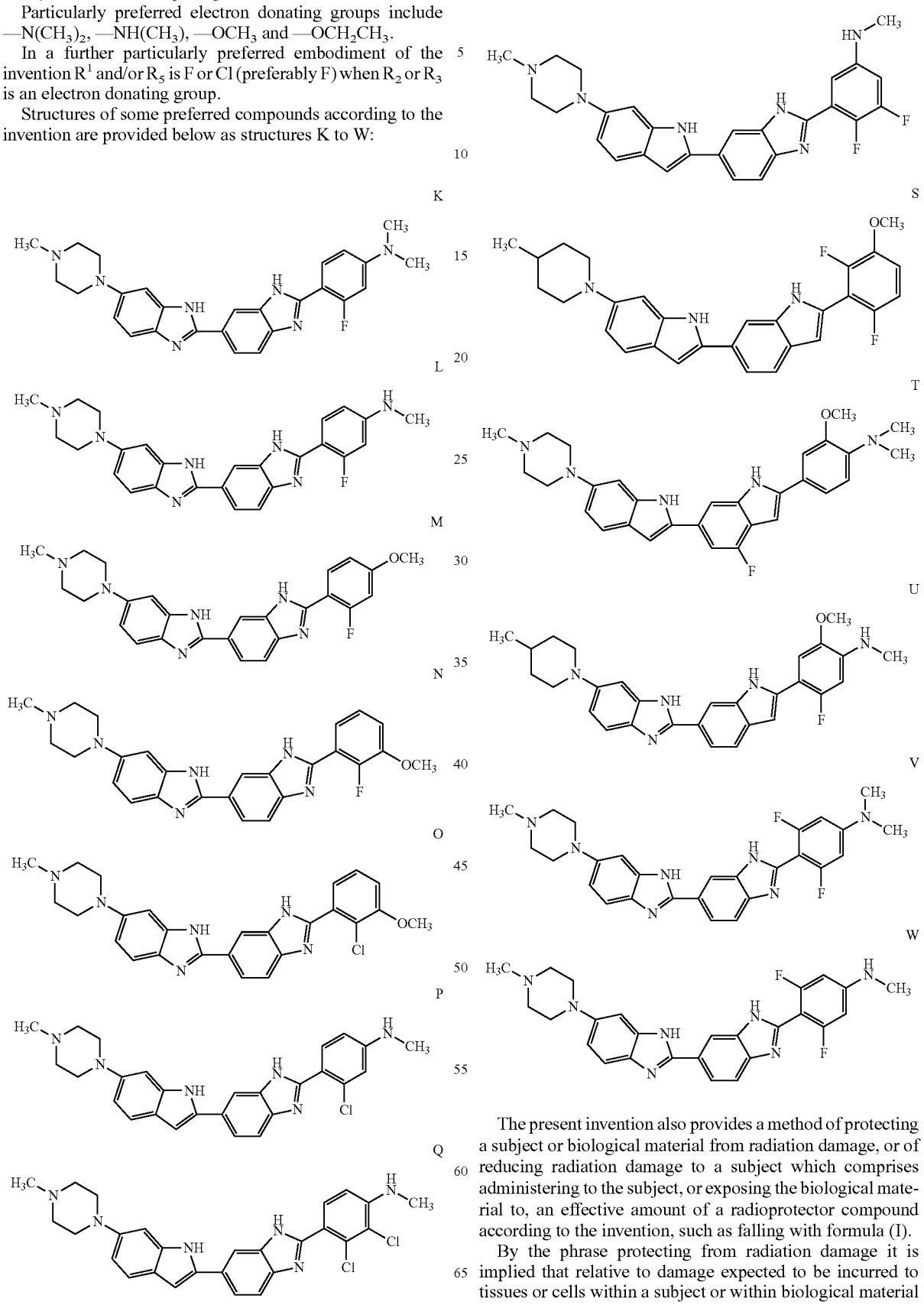

The present invention also provides a method of protecting a subject or biological material from radiation damage, or of reducing radiation damage to a subject which comprises administering to the subject, or exposing the biological material to, an effective amount of a radioprotector compound according to the invention, such as falling with formula (I).

By the phrase protecting from radiation damage it is implied that relative to damage expected to be incurred to tissues or cells within a subject or within biological material following exposure to a given amount of radiation (for example ionising, infra-red or ultra-violet radiation) damage is prevented, minimised or reduced due to presence of the radioprotector compound. The term "Dose Modification Factor" (DMF) refers to the ratio of the radiation dose required to produce a given effect in the presence of protector, to that required to produce the equivalent effect in the absence of protector.

The radiation damage may result from exposure to a radiation source, such as, ionising radiation. The term "ionising radiation" as used herein refers to photons having enough energy to ionise a bond, such as, α, β and γ rays from radioactive nuclei and x-rays.

The term "biological material" is used herein in its broadest sense and includes any composition of matter which comprises at least one biologically-derived or derivable component. Biological material contemplated by the present invention includes proteins and other proteinaceous material including extracts of or including proteins and chemically modified proteins or extracts thereof; tissue fluids, tissue extracts or organs; animal, plant or microbiological tissue, fluid or extracts including products therefrom; biologically derived non-proteinaceous material such as, but not limited to, lipids, carbohydrates, hormones and vitamins including extracts and derivatives thereof; recombinant products including genetic material such as chromosomal material, genomic DNA, cDNA, mRNA, tRNA, ribosomes and nuclear material; and whole animal, plant or microbiological cells or extracts thereof.

As indicated the biological material of the invention can take the form of cells, tissues or organs or indeed of peptides, proteins or nucleic acids (for example) derived from a plant, animal or microorganism source, as well as those synthetically produced which mimic or are similar to naturally derived materials. The radioprotector compound can be used to protect from radiation damage for example in experimental systems, in whole live or dead organisms or on ex vivo cells, tissues or organs that may be returned to the original host, or transplanted into a new host, after therapy.

For example, the biological material can take the form of a human or animal subject such as an experimental animal (eg. mouse, rat, guinea pig, rabbit), a companion animal (eg. cat, dog), an agricultural animal (eg. horse, cattle, sheep, donkey, goat, pig), a reptile, avian or captive wild animal. Preferably the subject is a mammal and most preferably the subject is a human. A significant application for the radioprotector compounds of the invention is for use in conjunction with radiotherapy in human subjects. However, the compounds can also be used to offer protection from exposure to, or from continuing exposure to, unplanned radiation such as in a terrorism, military or occupational context.

Preferably the biological material (including to the human or animal subject) is exposed to the radioprotector compound for a sufficient period of time in advance of anticipated radiation exposure or continuing radiation exposure, such as between about 1 minute and about 3 days, preferably between about 10 minutes and about 6 hours, more preferably between about 20 minutes and about 4 hours and most preferably between about 30 minutes and about 2 hours. Preferably the time of administration of the radioprotector compound prior to radiation exposure is sufficient to allow association of the compound with DNA in the biological material. Preferably the radioprotector compound is administered preferentially to cells, tissues or organs likely to be exposed to radiation but that are intended to be protected from such radiation exposure. For example, in the case of administration in conjunction with cancer radiotherapy the compounds will preferably be administered preferentially to normal (non-tumour) tissues or cells surrounding a tumour or lesion that are likely to be exposed to radiation in the course of radiotherapy. Preferential administration can be achieved by way of direct application to the desired tumour or cells or, for example, by utilising a system for targeting specific cells or tissues. For example it is possible to conjugate the compounds to agents that preferentially bind to specific cells or tissues, such as to receptors that are up-regulated in the particular cells or tissues concerned.

The compounds of the invention may be conjugated to agents, for example, via an interactive group, which will specifically deliver them to a desired tumour site. Suitable agents may include antibodies or proteins, such as, growth factors, for example, haemopoietic growth factor which will enable preferential radioprotection of haemopoietic stem cells to occur in the context of total body irradiation and bone marrow transplantation. The term "interactive group" is used herein in its broadest sense and refers to a group capable of forming a bond with a specific group on a target molecule or agent such as a protein or a derivative thereof. Examples of interactive groups include $N(CH_2)_nCOOH$, $N(CH_2)_nCO(CH_2)_mR$, $N(CH_2)_n$—SH, $N(CH_2)_n$—$NH_2$, $CH(CH_2)_nCOOH$, $CH(CH_2)_nCO(CH_2)_nR$, $CH(CH_2)_n$—SH and $CH(CH_2)_n$—$NH_2$ wherein n is 1 to 10, m is 0 to 10 and R is optionally substituted alkyl.

The present invention still further provides a method of cancer radiotherapy which comprises administering to a subject in need of such therapy an effective amount of a radioprotector compound of the invention and subjecting the locus of the tumour to a radiation source. The term "cancer radiotherapy" is used herein in its broadest sense and includes radiotherapy involving tumours or lesions, which may be either benign or malignant.

The compounds of the invention may be used advantageously in therapy in combination with other medicaments, such as chemotherapeutic agents, for example, radiomimetic agents which are cytotoxic agents that damage DNA in such a way that the lesions produced in DNA are similar to those resulting from ionising radiation. Examples of radiomimetic agents which cause DNA strand breaks include bleomycin, doxorubicin, adriamycin, 5FU, neocarcinostatin, alkylating agents and other agents that produce DNA adducts. It is anticipated that the radioprotectors of the present invention will protect DNA from damage by some of these agents, in the same way as they protect against the effects of ionising radiation. In clinical applications, it is unlikely that the radioprotector would be administered systemically together with the chemotherapeutic agent, since this could compromise the action of this agent on the tumour. However, there are circumstances where topical application to problem tissues could be advantageous. For example, oral mucositis is a problem side-effect for cytotoxic agents, such as, doxorubicin and administration of the present radioprotector as a mouth-wash before administration of the chemotherapeutic agent could ameliorate this side-effect without compromising the action of this agent on a tumour not located in the oral cavity. Similarly, the gastrointestinal tract could be protected by oral administration, the lungs by aerosol inhalation or the bladder by intravesical delivery, for example, via a catheter of the radioprotector. Hence a preferred method in accordance with the present invention utilises the compound of formula (I) in conjunction with another medicament, such as, a radiomimetic agent.

As earlier mentioned there is an ex vivo application of the compounds or conjugates of the invention and one example is in the context of bone marrow transplantation. Bone marrow transplantation generally involves obtaining and storing bone marrow samples from a subject in anticipation of a deterioration of their condition. A rather drastic form of chemotherapy (i.e. a high dose) is then administered. This chemotherapy is such that it would normally be lethal due to the destruction of normal stem cells, but the subject is rescued by the administration of their own haemopoietic stem cells. The problem with this procedure is that the initial sample of stem cells is likely to be contaminated with tumour cells and various procedures are used therefore to purge the bone marrow preparations of the tumour cells. Radioprotectors conjugated for example to a haemopoietic growth factor, may be used in this context by being added to a suspension of bone marrow cells. The suspension may then be irradiated in the expectation that the normal bone marrow cells, but not the tumour cells, would be preferentially protected from the cell-killing effects of the radiation.

The compounds of formula (I) may be administered for therapy by any suitable route, including oral, rectal, nasal, topical (including buccal and sublingual), vaginal, intravesical and parenteral (including subcutaneous, intramuscular, intravenous, intrasternal and intradermal). Preferably, administration will be by the rectal, topical, vaginal or parenteral route, however it will be appreciated that the preferred route will vary with the condition and age of the subject, the tissue/tumour being treated, its location within the subject and the judgment of the physician or veterinarian. The compound of formula (I) may be administered directly into tissues surrounding or proximal to tumours to be irradiated.

The present invention also extends to a radioprotective composition which comprises a compound of formula (I) as defined above (also referred to as "compound of the invention", "active agent", "active ingredient" or "radioprotector compound") in association with a pharmaceutically or veterinarily acceptable carrier.

The compositions of the present invention comprise at least one compound of formula (I) together with one or more pharmaceutically acceptable carriers, diluents, adjuvants and/or excipients and optionally other medicaments. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal, intravesical or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product. Further details of conventional pharmaceutical compositions are explained in Remington's Pharmaceutical Sciences, 18$^{th}$ Edition, Mack Publishing Co., Easton, Pa., USA, the disclosure of which is included in its entirety by way of reference.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or as granules, optionally mixed with a binder (e.g. cross-linked povidone, cross-linked sodium carboxymethyl cellulose), inert diluent, preservative, disintegrant (e.g. sodium starch glycollate), surface-active agent and/or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured basis, usually sucrose and acacia or tragacanth gum; pastilles comprising the active ingredient in an inert basis such as gelatin and glycerin, or sucrose and acacia gum; and mouthwashes or sprays comprising the active ingredient in a suitable liquid carrier.

For topical application to the skin, the active ingredient may be in the form of a cream, ointment, jelly, solution or suspension.

For topical application to the eye, the active ingredient may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

Compositions for rectal administration may be presented as a suppository with a suitable non-irritating excipient which is solid at ordinary temperatures but liquid at the rectal temperature and will therefore melt in the rectum to release the active ingredient. Such excipients include cocoa butter or a salicylate.

Nasal compositions may be presented topically as nose drops or sprays or systemically in a form suitable for absorption through the nasal mucosa and/or the alveolar cells in the lungs.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of an active ingredient. The compounds of the invention may be administered for example in amounts of between about 0.01 mg to about 500 mg per kg body weight of the subject per day (or preferably per incidence of radiation exposure), preferably between about 0.1 mg to about 100 mg, more preferably between about 1.0 mg to about 10 mg per kg body weight of the subject per day or per incidence of radiation exposure.

The compound of formula (I) may also be presented for use in the form of veterinary compositions, which may be prepared, for example, by methods that are conventional in the art. Examples of such veterinary compositions include those adapted for:
  (a) oral administration, external application, for example drenches (e.g. aqueous or non-aqueous solutions or suspensions); tablets or boluses; powders, granules or pellets for admixture with feed stuffs; pastes for application to the tongue;
  (b) parenteral administration for example by subcutaneous, intramuscular or intravenous injection, e.g. as a sterile solution or suspension; or (when appropriate) by intramammary injection where a suspension or solution is introduced into the udder via the teat;
  (c) topical application, e.g. as a cream, ointment or spray applied to the skin; or
  (d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

An important application of the radioprotector of the present invention is in cancer radiotherapy. Many of the normal tissues which are a problem in radiotherapy such as the skin, oral mucosa, oesophageal mucosa, rectal mucosa, vaginal mucosa and bladder epithelium can be topically protected by the radioprotectors of the present invention.

There are two distinct settings for such topical radioprotectors. Firstly, there is potential to decrease the distressing acute reactions that often occur in the normal tissues noted above. Although these acute reactions can be transient, their amelioration will obviously be of benefit to a subject. A different setting is the situation where acute reactions limit the dose of radiation that can be delivered to the tumour. An example is in the accelerated fractionation regime, in which acute reactions can be dose-limiting. Thus, the application of radioprotectors can enable the use of higher radiation doses, and hence improve prospects for cure.

Aside from topical application, the pharmaco-distribution properties of the radioprotectors of the present invention offer other ways of achieving an improved therapeutic ratio. Examples include tumours in the brain and lung.

In the case of the brain, endothelial cells are thought to be an important radiosensitive target in terms of the detrimental effects of radiation on normal brain tissue. The administration of the radioprotector of the present invention would protect the important endothelial cells in the normal brain. The corresponding cells in the tumour would also be protected, but these cells are well oxygenated and therefore are the most radiosensitive cells in the tumour. The more distant cells in the tumour, which are hypoxic, would therefore be out of reach of the radioprotector, if administered at an appropriate interval prior to irradiation. This means that the normal endothelial cells and oxic (radiosensitive) cells of the tumour would be protected equally. This radioprotection would then enable a higher dose of irradiation to be used which would increase the chance of killing the hypoxic cells in the tumour. The fact that the endothelial cells of both the tumour and normal tissue are effected equally has no impact on the therapeutic ratio. An increase in the therapeutic ratio could result because of the increase in kill of hypoxic tumour cells, without any debt in terms of normal tissue damage.

In the case of tumours in the lung, the radioprotector of the present invention would be delivered to alveolar cells. Although the endothelial cells of the lung tumour may also be protected, the more distant cells in the tumour would not. Moreover, the circulation of some lung tumours is provided not by the pulmonary artery but from the bronchial circulation, which will not be accessed until the next pass of the radioprotector in the circulation and hence exposed to lower concentrations.

The targeting of radioprotectors may also achieve improved therapeutic ratios in radiotherapy. A suitable example is the conjugation of the radioprotector of the present invention to haemopoietic growth factor to achieve preferential radioprotection of haemopoietic stem cells in the context of total body irradiation and bone marrow transplantation.

Outside the context of cancer radiotherapy, the radioprotectors of the present invention can be used prophylactly in high risk radiation situations. For example, the haemopoietic growth factor conjugate described above may be administered for this purpose. More generally, radioprotectors represented by formula (I) can be used prophylactically in situations where there is a risk of exposure to radiation, or to mitigate against the effects of continuing exposure. In such situations, the compounds may be administered parentally (preferably subcutaneously) or orally, without any consideration for the concern associated with the cancer radiotherapy setting, namely delivery of the radioprotector to the tumour.

Compounds of formula (I) as referred to above can be prepared in accordance with Scheme 1, as follows:

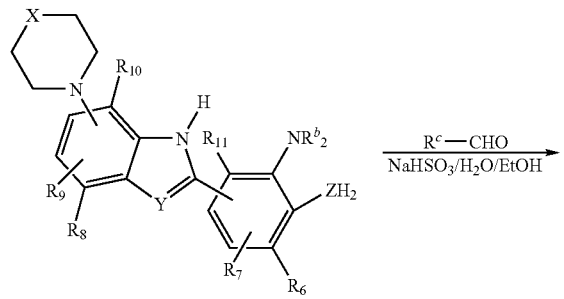

Within Scheme 1, X, Y, Z and $R_1$ to $R_{11}$ are as hereinbefore defined in relation to Formula I and $R^c$ represents:

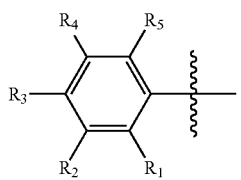

In Scheme 1 $R^b$ initially represents O. This nitroamine compound (an example of which has previously been reported by Kelly et al (5)) is reduced to the diamine, for example by catalytic hydrogenation, wherein $R^b$ represents H. The diamine is then immediately coupled to the desired aldehyde in the presence of metabisulphite to produce the intended bis-benzimidazole. Specific examples of compounds produced according to Scheme 1 are provided below.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention will now be described with reference to the following Examples. These Examples are not to be construed as limiting the invention in any way.

Synthesis of fluorinated or chlorinated bis-benzimidazoles

The fluorinated or chlorinated DNA ligands of examples (1)-(10) were prepared according to the general scheme outlined in Scheme 2. Nitroamine precursor ($P_O$), the preparation of which has been previously reported[5], was reduced by catalytic hydrogenation to the corresponding precursor diamine ($P_H$) which was then immediately coupled to the aldehydes (i)-(x) in the presence of metabisulphite, furnishing in good yield, the bis-benzimidazoles (1)-(10), respectively.

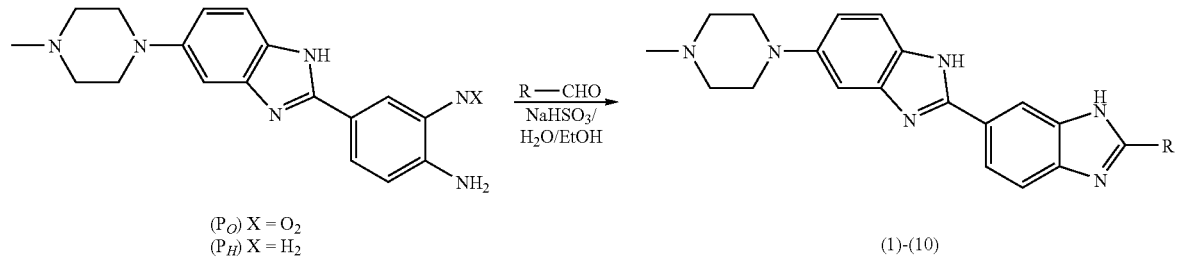

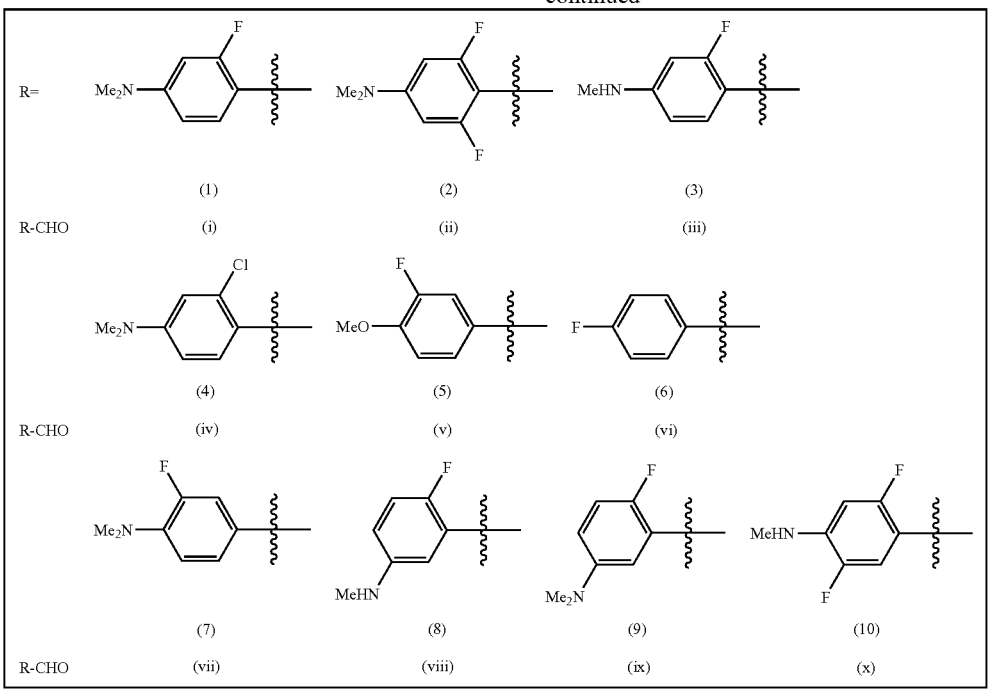

Methods

Melting points were determined using an Electrothermal melting point apparatus, and are uncorrected. Proton ($^1$H) and carbon ($^{13}$C) nuclear magnetic resonance (nmr) spectroscopy were recorded as solutions in the stated solvent using a Varian Inova 400 or Varian Inova 500 spectrometer, at 399.77 or 499.69 MHz respectively for $^1$H, and at 100.52 or 125.66 MHz respectively for $^{13}$C. $^1$H nmr spectra were measured as chemical shifts quoted in parts per million (ppm) from tetramethylsilane, followed by multiplicity, coupling constant(s), number of equivalent nuclei, and assignment. The abbreviations s for singlet, d for doublet, t for triplet, q for quartet, br for broad and m for multiplet were used in the assignments of multiplicity. A value approximating the centre of a multiplet is quoted. The addition of a few drops of trifluoroacetic acid-d (d-TFA) to methanol-d4 solutions was found to reduce peak broadening and enhance the definition of multiplets in the aromatic region. The addition of a few drops of acetic acid to methanol-d4 solutions was used to enhance solubility for the acquisition of $^{13}$C nmr spectra. Mass spectra were recorded on a Micromass Quattro II mass spectrometer and accurate mass analyses were carried out by the School of Chemistry at the University of Melbourne on a Finnigan LTQ-FT model high resolution mass spectrometer. Thin layer chromatography (TLC) was carried out using Merck silica gel 60 $F_{254}$ aluminium sheets or Merck neutral aluminium oxide 150 $F_{254}$ sheets. Flash column chromatography was carried out using Ajax silica gel 230-400 mesh.

The nitrobenzimidazole ($P_O$) was prepared as reported previously by Kelly et al[5].

Example 1

Preparation of 4-dimethylamino-2-fluoro-1-(5'-(5"-(4'"-methylpiperazin-1'"-yl)benzimidazol-2"-yl)benzimidazol-2'-yl)benzene (1)

To a solution of 4-dimethylamino-2-fluorobenzaldehyde (i) (1.98 g, 11.8 mmol) in ethanol (35 ml) was added a solution of sodium metabisulfite (2.6 g, 13.7 mmol) in 1:1 ethanol/water (40 ml) and the mixture was warmed for 10 min. A solution of diamine ($P_H$) (from catalytic hydrogenation of 3.22 g of nitroamine ($P_O$), 9.14 mmol) in ethanol (50 ml) was then added and the mixture was refluxed under nitrogen for 21 h. The condenser was then replaced with a stillhead and approx 50 ml of reaction solvent was removed by distillation. The remaining reaction mixture was then cooled to −20° and the yellow solid was collected and carefully washed with dilute ammonia solution (6%, 50 ml), water (50 ml), acetone (2×20 ml) and ether (50 ml) before being dried under vacuum to give 4-dimethylamino-2-fluoro-1-(5'-(5"-(4'"-methylpiperazin-1'"-yl)benzimidazol-2"-yl)benzimidazol-2'-yl)benzene (1) as a pale yellow powder (2.50 g, 58%), which was further purified by recrystallization from ethanol, mp≥240°.

$^1$H nmr (500 MHz, $d_4$-MeOH+2 drops d-TFA) δ 3.01, s, 3H, 4'"-MeN; 3.16, s, 6H, 4-Me$_2$N; 3.20, t (J=11.5 Hz), 2H, NCH$_2$; 3.34, dt (J=3.0, 13.0 Hz), 2H, NCH$_2$; 3.69, d (J=12.0 Hz), 2H, NCH$_2$; 3.98, d (J=13.5 Hz), 2H, NCH$_2$; 6.75, dd (J=2.5, 16.0 Hz), 1H, H3; 6.84, dd (J=2.5, 9.5 Hz), 1H, H5; 7.35, d (J=2.0 Hz), 1H, H4"; 7.45, dd (J=2.5, 9.0 Hz), 1H, H6"; 7.76, d (J=9.0 Hz), 1H, H7"; 7.97, app t (J=9.0 Hz), 1H, H6; 8.02, d (J=8.5 Hz), 1H, H7'; 8.21, dd (J=1.5, 8.7 Hz), 1H, H6'; 8.50, d (J=1.5 Hz), 1H, H4'. $^{13}$C nmr (100 MHz, $d_4$-MeOH+3 drops HOAc) δ 39.9, 4-Me$_2$N; 43.6, 4'"-MeN; 49.3, C2'"/6'"; 54.6, C3'"/5'"; 98.7, d ($^2J_{CF}$=26 Hz), C3; 102.1, C4"; 102.9, d ($^2J_{CF}$=11 Hz), C1; 109.0, C5; 113.2, C4'; 115.6, C7'; 116.1, 116.5, C6", C7"; 122.3, C6'; 123.0, C5'; 131.0, d ($^3J_{CF}$=3 Hz), C6; 133.8, C7a"; 138.4, 138.6, C3a', C3a"; 140.3, C7a'; 148.5, C5"; 150.8, 152.5, C2', C2"; 154.6, d ($^3J_{CF}$=12 Hz), C4; 162.7, d ($^1J_{CF}$=246 Hz), C2. MS (ESI+ve) m/z 470 (M+H, 50%). HRMS (ESI+ve) m/z 470.2461, $C_{27}H_{29}FN_7$ requires 470. 2463 (Δ=0.4 ppm).

Example 2

Preparation of 2,6-difluoro-4-dimethylamino-1-(5'-(5"-(4'''-methylpiperazin-1'''-yl)benzimidazol-2"-yl)benzimidazol-2'-yl)benzene (2)

A solution of 2,6-difluoro-4-dimethylaminobenzaldehyde (ii) (0.20 g, 1.1 mmol) in ethanol (10 ml) was treated with a solution of sodium metabisulfite (0.246 g, 1.3 mmol) in water (1 ml), and the combined mixture was then added to a solution of the diamine ($P_H$) (0.29 g, 0.9 mmol) in ethanol (14 ml), and was refluxed under nitrogen for 24 h. The reaction mixture was cooled, the solvents removed by rotary evaporator and the residue was treated with dilute ammonia solution (6%, 2×20 ml), acetonitrile (2×20 ml) and ether (2×20 ml) with each treatment followed by centrifugation and removal of the supernatant. Drying of the resultant solid under vacuum afforded 2,6-difluoro-4-dimethylamino-1-(5'-(5"-(4'''-methylpiperazin-1'''-yl)benzimidazol-2"-yl)benzimidazol-2'-yl)benzene (2) as a light tan powder (0.362 g, 82%), mp 259-261°.

$^1$H nmr (500 MHz, $d_4$-MeOH+3 drops d-TFA) δ 3.02, s, 3H, 4'''-MeN; 3.17, s, 6H, 4-Me$_2$N; 3.23, t (J=12 Hz), 2H, NCH$_2$; 3.36, m (obscured), NCH$_2$; 3.70, d (J=12.0 Hz), 2H, NCH$_2$; 3.99, d (J=13.5 Hz), 2H, NCH$_2$; 6.69, d (J=14.5 Hz), 2H, H3/5; 7.34, d (J=2.0 Hz), 1H, H4"; 7.45, dd (J=2.0, 9.5 Hz), 1H, H6"; 7.77, d (J=9.0 Hz), 1H, H7"; 8.06, d (J=8.5 Hz), 1H, H7; 8.25, dd (J=1.5, 9.0 Hz), 1H, H6'; 8.56, d (J=1.5 Hz), 1H, H4'. $^{13}$C nmr (100 MHz, $d_4$-MeOH+3 drops HOAc) δ 40.0, 4-Me$_2$N; 43.6, 4'''-MeN; 49.4, C2'''/6'''; 54.6, C3'''/5'''; 94.4, t ($^2J_{CF}$=16 Hz), C1; 95.8, d ($^2J_{CF}$=28 Hz), C3/5; 102.4, C4"; 113.9, C4'; 116.1, 116.4, 116.6, C6", C7', C7"; 122.6, C6'; 124.0, C5'; 134.7, C7a"; 139.0, 139.2, C3a', C3a"; 140.5, C7a'; 146.5, C2' or C2"; 148.5, C5"; 153.1, C2" or C2'; 154.0, t ($^3J_{CF}$=14 Hz), C4; 162.9, dd ($^3J_{CF}$=10 Hz, $^1J_{CF}$=248 Hz), C2/6. MS (ESI+ve) m/z 488 (M+H, 10%).

Example 3

Preparation of 2-fluoro-4-methylamino-1-(5'-(5"-(4'''-methylpiperazin-1'''-yl)benzimidazol-2"-yl)benzimidazol-2'-yl)benzene (3)

A solution of 2-fluoro-4-methylaminobenzaldehyde (iii) (0.10 g, 0.65 mmol) in ethanol (10 ml) was treated with a solution of sodium metabisulfite (0.15 g, 0.8 mmol) in water (5 ml) and the mixture was heated gently for 10 min. A solution of the diamine ($P_H$) (0.16 g, 0.5 mmol) in ethanol (16 ml) was added and the mixture was refluxed under nitrogen for 21.5 h. The reaction mixture was cooled, filtered, and the filtered solid was washed with dilute ammonia solution (6%, 2×10 ml), acetone (2×10 ml), ether (2×10 ml), then dried under vacuum to give 2-fluoro-4-methylamino-1-(5'-(5"-(4'''-methylpiperazin-1'''-yl)benzimidazol-2"-yl)benzimidazol-2'-yl)benzene (3) as a tan powder (0.165 g, 73%).

$^1$H nmr (500 MHz, $d_4$-MeOH+3 drops d-TFA) δ 2.91, s, 3H, 4-MeN; 3.01, s, 3H, 4'''-MeN; 3.20, t (J=12 Hz), 2H, NCH$_2$; 3.34, m (obscured), NCH$_2$; 3.69, d (J=11 Hz), 2H, NCH$_2$; 3.98, d (J=13 Hz), 2H, NCH$_2$; 6.59, dd (J=2.0, 15.0 Hz), 1H, H3; 6.70, dd (J=2.5, 9.0 Hz), 1H, H5; 7.35, d (J=2.0 Hz), 1H, H4"; 7.45, dd (J=2.5, 9.0 Hz), 1H, H6"; 7.76, d (J=9.0 Hz), 1H, H7"; 7.89, app t (J=8.8 Hz), 1H, H6; 8.01, d (J=8.5 Hz), 1H, H7'; 8.21, dd (J=1.5, 8.8 Hz), 1H, H6'; 8.49, d (J=1.0 Hz), 1H, H4'. $^{13}$C nmr (125 MHz, $d_4$-MeOH+1 drop HOAc) δ 29.9, 4-MeHN; 44.3, 4'''-MeN; 50.1 C2'''/6'''; 55.1, C3'''/5'''; 98.4, d ($^2J_{CF}$=25 Hz), C3; 102.6, C4"; 18 Hz), C1; 110.0, C5; 113.7, C4'; 115.8, C7'; 116.39, 116.43, C6", C7"; 122.3, C6'; 124.6, C5'; 131.5, d ($^3J_{CF}$=7 Hz), C6; 135.5, C7a"; 139.77, 139.85, C3a', C3a"; 141.2, C7a'; 148.6, C5"; 151.8, 153.7, C2', C2"; 155.4, d ($^3J_{CF}$=12 Hz), C4; 163.4, d ($^1J_{CF}$=248 Hz), C2. MS (ESI+ve) m/z 456 (M+H, 25%). HRMS (ESI+ve) m/z 456.2306, $C_{26}H_{27}FN_7$ requires 456.2306 (Δ=0.0 ppm).

Example 4

Preparation of 2-chloro-4-dimethylamino-1-(5'-(5"-(4'''-methylpiperazin-1'''-yl)benzimidazol-2"-yl)benzimidazol-2'-yl)benzene (4)

Nitroamine ($P_N$) (0.115 g, 0.327 mmol) in 20% MeOH/EtOAc (20 ml) was hydrogenated in presence of 5% Pd/C at atmospheric pressure. After 3 hours the catalyst was removed by filtration through celite and the filtrate evaporated. The diamine residue was then shielded from light and kept under nitrogen. Sodium metabisulfite (0.327 mmol) in 1:1 EtOH/H$_2$O (3 ml) was added to 2-chloro-4-dimethylaminobenzaldehyde (iv) (0.06 g, 0.327 mmol) in EtOH (3 ml). The diamine ($P_H$) in EtOH (3 ml) was then added to the aldehyde/metabisulfite complex and the mixture stirred under reflux for 4 hours. The resulting mixture was cooled at 0° C. for 3 days and the resulting precipitate isolated by filtration giving (4) (0.1 g) as a brown powder.

$^1$H nmr (500 MHz, $d_4$-MeOH+3 drops d-TFA) δ 3.00, s, 3H, MeN; 3.14, s, 6H, Me$_2$N 3.23, t (J=12.0 Hz), 2H, NCH$_2$; 3.34, m (obs), 2H, NCH$_2$; 3.68, d (J=11.0 Hz), 2H, NCH$_2$; 3.98, d (J=14.0 Hz), 2H, NCH$_2$; 6.93, dd, (J=2.0, 8.5 Hz), 1H, H5, 7.00, d, (J=2.0 Hz), 1H, H3; 7.40, bs, 1H, H4"; 7.44, dd (J=2.0, 8.5 Hz), 1H, H6"; 7.77, d (J=8.8 Hz), 1H, H7"; 7.84, d, (J=9.0 Hz), 1H, H5; 8.08, d (J=8.8 Hz), 1H, H7; 8.26, dd (J=2.0, 8.5 Hz), 1H, H6'; 8.59, d (J=1.5 Hz), 1H, H4'. HRMS (ESI+ve) m/z 486.2162 calc=416.2168, (Δ=1.2 ppm).

Example 5

Preparation of 3-fluoro-4-methoxy-1-(5'-(5"-(4'''-methylpiperazin-1'''-yl)benzimidazol-2"-yl)benzimidazol-2'-yl)benzene (5)

Nitroamine ($P_O$) (0.45 g, 1.3 mmol) in 20% MeOH/EtOAc (20 ml) was hydrogenated in the presence of 5% Pd/C at atmospheric pressure. After 5 hours the catalyst was removed by filtration and the filtrate evaporated to give the diamine ($P_H$) as an orange residue. Sodium metabisulphite (0.49 g, 2.6 mmol) in 1:1 EtOH/H$_2$O (20 ml) was added to 3-fluoro-4-methoxybenzaldehyde (v) (0.40 g 2.6 mmol) in EtOH (20 ml). The freshly prepared diamine ($P_H$) in EtOH (40 ml) was added to the aldehyde/metabisulphite complex and the mixture refluxed under nitrogen for 20 hours. The mixture was evaporated and the resulting residue washed with Et$_2$O and hot chloroform. The resulting solid was dissolved in minimum EtOH, then treated with Et$_2$O, the solid obtained by filtration was then dissolved in 1N HCl and reprecipitated by the addition of 28% NH$_3$ solution. Filtration gave (5) as a brown powder (0.128 g).

$^1$H nmr (500 MHz, $d_4$-MeOH+3 drops d-TFA) δ 3.01, s, 3H, MeN; 3.22, t (J=12.0 Hz), 2H, NCH$_2$; 3.33, m, 2H, NCH$_2$; 3.69, d (J=12 Hz), 2H, NCH$_2$; 3.97, d (J=13.2 Hz), 2H, NCH$_2$; 4.04, s, 3H, OCH$_3$; 7.36, d (J=2.2 Hz), 1H, H4"; 7.42, dd (J=2.2, 9.3 Hz), 1H, H6"; 7.47, app t (J=9.0 Hz), 1H, H4; 7.76, d (J=9.0 Hz), 1H, H7"; 8.00, dd (J=11.5, 2.1 Hz), 1H, H2; 8.05, dd, (J=8.8, 1.5 Hz), 1H, H5; 8.08, d, (J=8.5 Hz), 1H, H7' 8.25, dd (J=1.8, 8.6 Hz), 1H, H6'; 8.58, d (J=1.7 Hz), 1H, H4'. $^{13}$C nmr (125 MHz, $d_4$-MeOH+1 drop HOAc) δ 43.6, 4'''-MeN; 48.6 C2'''/6'''; 54.6, C3'''/5'''; 56.6 (OMe); C3; 101.3, C4"; 114.1, 114.3, 115.07 (C3, $^3J_{CF}$=21 Hz) 115.7 (ArCH), 116.5 (ArCH), 117.3 (ArCH), 120.2, (C5'/C1); 121.9 (C5'/C1); 122.3 (C6'); 124.3 (C6); 130.7 (C7a"), 136.3 (C3a'/C3a"); 142.0 (C7a'); 149.0 (C5"); 150.82 ($^4J_{CF}$=10 Hz) (C4); 151.0 (C2"/C2'); 153.05 ($^1J_{CF}$=245 Hz) (C3); 153.9 (C2'/C2"). HRMS (ESI+ve) m/z=457.2140, calc=457.2149, (Δ=2.0 ppm).

Example 6

4-fluoro-1-{5'-[5"-(4'''-methylpiperazin-1'''-yl)benzimidazol-2"-yl]benzimidazol-2'-yl}benzene (6)

Nitroamine ($P_O$) (0.500 g, 1.42 mmol) in 20% MeOH/EtOAc (20 ml) was hydrogenated in presence of 5% Pd/C at atmospheric pressure. After 5 hours the catalyst was removed by filtration through celite and the filtrate evaporated. The resulting residue was then shielded from light and kept under nitrogen. Sodium metabisulfite (0.437 g, 2.30 mmol) in 1:1 EtOH/H$_2$O (20 ml) was added to 4-fluorobenzaldehyde (vi) (0.29 g, 2.30 mmol) in EtOH (20 ml). The diamine ($P_H$) in EtOH (40 ml) was then added to the aldehyde/metabisulfite complex and the mixture stirred under reflux for 20 hours. The mixture was then let to cool down to room temperature for a few hours. After filtration, the solid obtained was washed with EtOH, diluted with HCl (1N) and reprecipitated with 28% NH$_{3liq}$ to give a pure (6) (0.230 g).

$^1$H nmr (500 MHz, d$_4$-MeOH+3 drops d-TFA) δ 3.01, s, 3H, MeN; 3.23, t (J=12.0 Hz), 2H, NCH$_2$; 3.34, m (obs), 2H, NCH$_2$; 3.69, d (J=11.5 Hz), 2H, NCH$_2$; 3.97, d (J=14.0 Hz), 2H, NCH$_2$; 7.35, d (J=2.0 Hz), 1H, H4"; 7.42, dd (J=2.3, 9.3 Hz), 1H, H6"; 7.48, app t (J=9.0 Hz), 2H, H3/5; 7.75, d (J=9.0 Hz), 1H, H7"; 8.07, d (J=8.5 Hz), 1H, H7'; 8.22, dd (J=2.0, 8.5 Hz), 1H, H6'; 8.26, dd (J=5.0, 9.0 Hz), 2H, H2/6; 8.58, d (J=1.5 Hz), 1H, H4'. HRMS (ESI+ve) m/z=428.2025, calc=428.2074, (Δ=13.8 ppm).

Example 7

Preparation of 4-dimethylamino-3-fluoro-1-(5'-(5"-(4'''-methylpiperazin-1'''-yl)benzimidazol-2"-yl)benzimidazol-2'-yl)benzene (7)

From Nitroamine ($P_O$) and 4-dimethylamino-3-fluorobenzaldehyde (vii), as per the method described for the preparation of (1) gave (7) as a pale yellow powder.

$^1$H nmr (500 MHz, d$_4$-MeOH+2 drops d-TFA) δ 2.99, s, 3H, MeN; 3.15, s, 6H, 4-Me$_2$N; 3.22, t (J=11.5 Hz), 2H, NCH$_2$; 3.34, m, 2H, NCH$_2$; 3.68, d (J=11.9 Hz), 2H, NCH$_2$; 3.96, d (J=13.5 Hz), 2H, NCH$_2$; 7.11, apt (J=8.5 Hz), 1H, H5; 7.37, d (J=2.0 Hz), 1H, H4"; 7.44, dd (J=2.5, 9.3 Hz), 1H, H6"; 7.76, d (J=9.0 Hz), 1H, H7"; 7.90, dd (J=2.0, 14.7 Hz), 1H, H2; 7.92, dd, (J=2.0, 9.0 Hz), 1H, H2; 8.03, d (J=8.5 Hz), 1H, H7'; 8.24, dd (J=1.5, 6.9 Hz), 1H, H6'; 8.54, d (J=1.5 Hz), 1H, H4'. HRMS (ESI+ve) m/z=470.2459 calc=470.2463, (Δ=0.8 ppm).

Example 8

Preparation of 2-fluoro-5-methylamino-1-(5'-(5"-(4'''-methylpiperazin-1'''-yl)benzimidazol-2"-yl)benzimidazol-2'-yl)benzene (8)

To a solution of 2-fluoro-5-methylaminobenzaldehyde (viii) (155 mg, 1.01 mmol) in ethanol (5 ml) was slowly added a solution of sodium metabisulfite (206 mg, 1.08 mmol) in water (1 ml). The resulting mixture was then added to a solution of the diamine (prepared from catalytic hydrogenation of 0.92 mmol of nitroamine $P_O$) in ethanol (5 ml), with additional ethanol (5 ml) used to aid the transfer. The mixture was refluxed under nitrogen for 16.5 h before cooling and removal of the solvent by rotary evaporator. The residue was treated with dilute ammonia solution (6%, 3×10 ml), acetonitrile (2×10 ml) and diethyl ether (2×10 ml) with centrifugation and removal of the supernatant following each treatment. Drying of the resultant solid under vacuum gave a light brown powder which was dissolved in 4:1 ethyl acetate/methanol (3 ml) and filtered through a plug of alumina (neutral, act. I, 40×40 mm) using the same solvent mixture, to give 2-fluoro-5-methylamino-1-(5'-(5"-(4'''-methylpiperazin-1'''-yl)benzimidazol-2"-yl)benzimidazol-2'-yl)benzene as a light orange-brown glassy solid (353 mg, 84%), mp 195-198° C.

$^1$H nmr (500 MHz, d$_4$-MeOH+4 drops d-TFA) δ 3.00, s, 3H, 5-MeN or 4'''-MeN; 3.02, s, 3H, 4'''-MeN or 5-MeN; 3.20, t (J=12.0 Hz), 2H, NCH$_2$; 3.34, m (obscured), NCH$_2$; 3.69, d (J=12.0 Hz), 2H, NCH$_2$; 3.97, d (J=13.5 Hz), 2H, NCH$_2$; 7.35, m, 2H, H4, H4"; 7.43, m, 2H, H3, H6"; 7.74, d (J=9.0 Hz), 1H, H7"; 7.77, dd (J=2.8, 5.8 Hz), 1H, H6; 8.04, d (J=9.0 Hz), 1H, H7'; 8.15, dd (J=8.5, 2.0 Hz), 1H, H6'; 8.55, d (J=1.5 Hz), 1H, H4'. $^{13}$C nmr (100 MHz, d$_4$-MeOH+3 drops HOAc) δ 31.0, 5-MeHN; 43.6, 4'''-MeN; 49.2, C2'''/6'''; 54.5, C3'''/5'''; 102.2, C4"; 112.0, C6; 114.6, C4'; 116.1, 116.5, 116.8, C6", C7', C7"; 117.4, d ($^3J_{CF}$=7 Hz), C4; 117.7, d ($^2J_{CF}$=23 Hz), C3; 117.8 (partially obs), C1; 122.6, C6'; 123.5, C5'; 133.8, C7a"; 138.6, 139.7, C3a', C3a"; 141.2, C7a'; 148.2, 148.5, C5, C5"; 151.0, 152.7, C2', C2"; 154.0, d ($^1J_{CF}$=238 Hz), C2. MS (ESI+ve) m/z 456 (M+H, 100%). HRMS (ESI+ve) m/z 456.23072, C$_{26}$H$_{27}$FN$_7$ requires 456.23065 (Δ=0.2 ppm).

Example 9

Preparation of 5-dimethylamino-2-fluoro-1-(5'-(5"-(4'''-methylpiperazin-1'''-yl)benzimidazol-2"-yl)benzimidazol-2'-yl)benzene (9)

To a solution of 5-dimethylamino-2-fluorobenzaldehyde (ix) (185 mg, 1.1 mmol) in ethanol (5 ml) was slowly added a solution of sodium metabisulfite (261 mg, 1.37 mmol) in water (1 ml) and the combined mixture then added to a suspension of the diamine (prepared from catalytic hydrogenation of 1.04 mmol of nitroamine $P_O$) in ethanol (5 ml), with additional ethanol (5 ml) used to aid the transfer. The mixture was then refluxed under nitrogen for 24 h before cooling and removal of the solvent by rotary evaporator. The residue was treated with dilute ammonia solution (6%, 2×15 ml), acetonitrile (2×10 ml) and diethyl ether (2×10 ml) with centrifugation and removal of the supernatant following each treatment. The resultant dried tan powder (467 mg) was recrystallized from methanol with hot filtration to give 5-dimethylamino-2-fluoro-1-(5'-(5"-(4'''-methylpiperazin-1'''-yl) benzimidazol-2"-yl)benzimidazol-2'-yl)benzene as a light tan powder (348 mg, 71%), mp 231-233° C.

$^1$H nmr (500 MHz, d$_4$-MeOH+3 drops d-TFA) δ 3.00, s, 3H, 4'''-MeN; 3.17, s, 6H, 5-Me$_2$N; 3.24, app t (J=13.0 Hz), 2H, NCH$_2$; 3.34, m (obscured), NCH$_2$; 3.68, d (J=12.0 Hz), 2H, NCH$_2$; 3.96, d (J=13.5 Hz), 2H, NCH$_2$; 7.34, d (J=2.0 Hz), 1H, H4"; 7.43, m, 3H, H3, H4, H6"; 7.74, d (J=9.0 Hz), 1H, H7"; 7.80, dd (J=3.0, 5.5 Hz), 1H, H6; 8.08, dd (J=0.8, 8.8 Hz), 1H, H7'; 8.20, dd (J=2.0, 8.5 Hz), 1H, H6'; 8.60, dd (J=1.8, 1.0 Hz), 1H, H4'. $^{13}$C nmr (100 MHz, d$_4$-MeOH+3 drops HOAc) δ 41.1, 5-Me$_2$N; 43.6, 4'''-MeN; 49.4, C2'''/6'''; 54.6, C3'''/5'''; 102.4, C4"; 113.4, C6; 114.6, C4'; 116.3, 116.5, 116.7, C6", C7', C7"; 117.3, d ($^3J_{CF}$=7 Hz), C4; 117.4 (partially obs), C1; 117.6, d ($^2J_{CF}$=23 Hz), C3; 122.7, C6'; 124.0, C5'; 134.4, C7a"; 139.0, 139.8, C3a', C3a"; 141.2, C7a'; 148.5, 149.0, C5, C5"; 151.0, 152.9, C2', C2"; 154.0, d ($^1J_{CF}$=239 Hz), C2. MS (ESI+ve) m/z 470 (MH$^+$, 100%). HRMS (ESI+ve) m/z 470.24612, C$_{27}$H$_{29}$FN$_7$ requires 470.24630 (Δ=0.4 ppm).

Example 10

Preparation of 2,5-difluoro-4-methylamino-1-(5'-(5"-(4'"-methylpiperazin-1'"-yl)benzimidazol-2"-yl)benzimidazol-2'-yl)benzene (10)

To a solution of 2,5-difluoro-4-methylaminobenzaldehyde (x) (250 mg, 1.46 mmol) in ethanol (16 ml) was added a solution of sodium metabisulfite (270 mg, 1.42 mmol) in water (1 ml) and the combined mixture then added to a suspension of the diamine (prepared from catalytic hydrogenation of 1.22 mmol of nitroamine, P$_O$) in ethanol (14 ml). The mixture was then refluxed under nitrogen for 16 h before cooling and removal of the solvent by rotary evaporator. The residue was treated with dilute ammonia solution (6%, 2×20 ml), acetonitrile (2×20 ml) and diethyl ether (2×20 ml) with centrifugation and removal of the supernatant following each treatment. The resulting solid was dried under vacuum to give 2,5-difluoro-4-methylamino-1-(5'-(5"-(4'"-methylpiperazin-1'"-yl)benzimidazol-2"-yl)benzimidazol-2'-yl)benzene (0.524 mg, 91%), mp 209-215° C.

$^1$H nmr (500 MHz, d$_4$-MeOH+3 drops d-TFA) δ 2.94, s, 3H, 4-MeN; 3.02, s, 3H, 4'"-MeN; 3.22, t (J=13 Hz), 2H, NCH$_2$; 3.34, m (obscured), NCH$_2$; 3.70, d (J=13 Hz), 2H, NCH$_2$; 3.97, d (J=13 Hz), 2H, NCH$_2$; 6.70, dd (J=7.2, 14.0 Hz), 1H, H3; 7.34, d (J=2.0 Hz), 1H, H4"; 7.42, dd (J=2.3, 9.3 Hz), 1H, H6"; 7.76, m, 2H, H6, H7"; 7.99, d (J=9.0 Hz), 1H, H7'; 8.18, dd (J=2.0, 8.5 Hz), 1H, H6'; 8.47, d (J=1.5 Hz), 1H, H4'.

Example 11

Preparation of Aldehydes a) Preparation of 2-fluoro-5-methylaminobenzaldehyde (viii)

Step 1: Preparation of 2-fluoro-5-methylaminobenzonitrile and 5-dimethylamino-2-fluorobenzonitrile

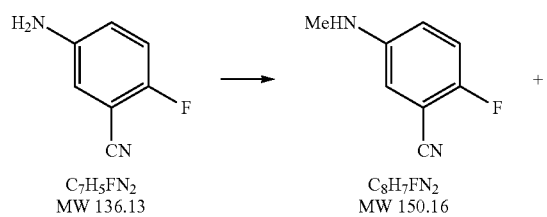

-continued

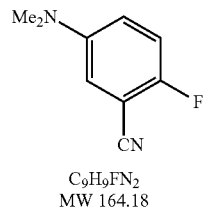

C$_9$H$_9$FN$_2$
MW 164.18

To a suspension of 5-amino-2-fluorobenzonitrile (2.50 g, 18.4 mmol) in methanol (100 ml) was added potassium carbonate (7.66 g, 55.4 mmol, 3 eq.) followed by methyl iodide (2.35 ml, 37.6 mmol, 2 eq.) and the mixture gently refluxed in a 65° oil bath under nitrogen for 23 h. Additional methyl iodide (4.7 ml, 4 eq.) was then added and refluxing continued for a further 23.5 h when all starting material had been consumed (as indicated by TLC-R$_f$ 0.09). The reaction mixture was concentrated and the residue partitioned between diethyl ether (100 ml) and water (100 ml). The aqueous layer was re-extracted with ether (100 ml) and the combined ether extract washed with water (100 ml), brine (100 ml), dried (MgSO$_4$) and evaporated to give an orange-brown oily solid (1.656 g). Column chromatography (neutral Al$_2$O$_3$ act I, 40×150 mm) eluting with 4:1 hexane/chloroform afforded 5-dimethylamino-2-fluorobenzonitrile (1.050 g, 35%) as a white solid, mp 72-72.5° C. Further elution with 3:2 hexane/chloroform afforded 2-fluoro-5-methylaminobenzonitrile (0.37 g, 13%) as an off-white solid, mp 64-65° C.

5-Dimethylamino-2-fluorobenzonitrile $^1$H nmr (500 MHz, CDCl$_3$) δ 2.94, s, 6H, NMe$_2$; 6.76, dd (J=3.3, 4.8 Hz), 1H, H6; 6.86, ddd (J=9.0, 4.0, 3.5 Hz), 1H, H4; 7.04, dd (J=8.5, 9.0 Hz), 1H, H3. $^{13}$C nmr (125 MHz, CDCl$_3$) δ 40.7, NMe$_2$; 101.0, d ($^2J_{CF}$=16 Hz), C1; 114.9, CN; 115.0, d ($^3J_{CF}$=3 Hz), C6; 116.6, d ($^2J_{CF}$=20 Hz), C3; 118.3, d ($^3J_{CF}$=6 Hz), C4; 147.0, C5; 155.3, d ($^1J_{CF}$=247 Hz), C2. MS (ESI+ve) m/z 165 (M+H, 100%). HRMS (ESI+ve) m/z 165.08220, C$_9$H$_{10}$FN$_2$ requires 165.08225 (Δ=0.1 ppm).

2-Fluoro-5-methylaminobenzonitrile $^1$H nmr (500 MHz, CDCl$_3$) δ 2.82, s, 3H, NMe; 3.87, br, 1H, NH; 6.68, app t (J=3.5 Hz), 1H, H6; 6.75, m, 1H, H4; 7.00, app t (J=8.8 Hz), 1H, H3. $^{13}$C nmr (125 MHz, CDCl$_3$) δ 30.7, NHMe; 101.1, d ($^2J_{CF}$=17 Hz), C1; 113.9, C6; 114.7, CN; 116.8, d ($^2J_{CF}$=21 Hz), C3; 118.7, d ($^3J_{CF}$=7 Hz), C4; 145.8, C5; 155.8, d ($^1J_{CF}$=246 Hz), C2. MS (ESI+ve) m/z 301 (2M+H, 60%), 151 (M+H, 100). HRMS (ESI+ve) m/z 151.06661, C$_8$H$_8$FN$_2$ requires 151.06660 (Δ=0.1 ppm).

Step 2: Preparation of 2-fluoro-5-methylaminobenzaldehyde (viii)

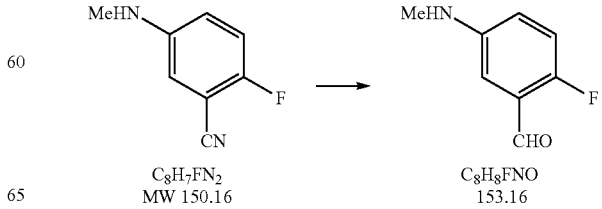

To a solution of 2-fluoro-5-methylaminobenzonitrile (307 mg, 2.04 mmol) in dry diethyl ether (10 ml) stirred at room temperature under nitrogen, was added dropwise by syringe diisobutylaluminium hydride (2.8 ml, 1.0 M in toluene, 2.8 mmol, 1.4 eq) and stirring continued for 19.5 h. The solution was chilled in an ice-bath and methanol (1.0 ml) was added dropwise and the mixture stirred for 1 h before 1.0 M HCl (9 ml) was added and stirring continued for a further 1 h. The reaction mixture was basified with NaOH (0.4 g) then partitioned between ether (50 ml) and water (50 ml) and the aqueous layer re-extracted with ether (50 ml). The combined ether extract was washed with brine (50 ml), dried over $MgSO_4$ and evaporated to give an orange oil (289 mg), which was subjected to column chromatography (silica gel, 30×190 mm) eluting with 100% dichloromethane, affording 2-fluoro-5-methylaminobenzaldehyde (viii) as a yellow crystalline solid (162 mg, 52%), mp 36-38° C.

$^1$H nmr (500 MHz, $CDCl_3$) δ 2.85, d (J=5.0 Hz), 3H, NMe; 3.77, br, 1H, NH; 6.82, ddd (J=9.0, 4.3, 3.3 Hz), 1H, H4; 6.97, dd (J=5.5, 3.0 Hz), 1H, H6; 7.00, app t (J=9.3 Hz), 1H, H3; 10.32, s, 1H, CHO. $^{13}$C nmr (100 MHz, $CDCl_3$) δ 31.0, NHMe; 108.6, C6; 116.9, d ($^2J_{CF}$=22 Hz), C3; 120.7, d ($^3J_{CF}$=8 Hz), C4; 124.0, d ($^2J_{CF}$=9 Hz), C1; 145.9, C5; 158.0, d ($^1J_{CF}$=248 Hz), C2; 187.0, d ($^3J_{CF}$=7 Hz), CHO. MS (ESI+ve) m/z 154 (M+H, 100%). HRMS (ESI+ve) m/z 154.06631, $C_8H_9FNO$ requires 154.06627 (Δ=0.3 ppm).

b) Preparation of 5-dimethylamino-2-fluorobenzaldehyde (ix)

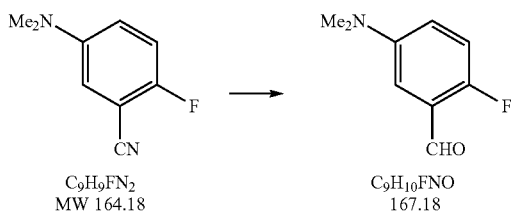 [SMILES: CN(C)c1ccc(F)c(C#N)c1 ; CN(C)c1ccc(F)c(C=O)c1]

C$_9$H$_9$FN$_2$
MW 164.18

C$_9$H$_{10}$FNO
167.18

To a solution of 5-dimethylamino-2-fluorobenzonitrile (viii) (331 mg, 2.02 mmol) in dry diethyl ether (10 ml) stirred at room temperature under nitrogen, was added dropwise by syringe diisobutylaluminium hydride (2.8 ml, 1.0 M in toluene, 2.8 mmol, 1.4 eq) and stirring continued for 19.5 h. The solution was chilled in an ice-bath and methanol (1.0 ml) was added dropwise and the mixture stirred for 1 h before 1.0 M HCl (9 ml) was added and stirring continued for a further 1 h. The reaction mixture was basified with NaOH (0.4 g) then partitioned between ether (50 ml) and water (50 ml) and the aqueous layer re-extracted with ether (50 ml). The combined ether extract was washed with brine (50 ml), dried over $MgSO_4$ and evaporated to give an orange oil (323 mg), which was subjected to column chromatography (silica gel, 30×170 mm) eluting with 100% dichloromethane, affording 5-dimethylamino-2-fluorobenzaldehyde (ix) as a bright yellow-green oil (228 mg, 68%).

$^1$H nmr (400 MHz, $CDCl_3$) δ 2.94, s, 6H, NMe$_2$; 6.93, dt (J=8.8, 4.0 Hz), 1H, H4; 7.03, app t (J=9.4 Hz), 1H, H3; 7.07, dd (J=3.4, 5.4 Hz), 1H, H6; 10.32, s, 1H, CHO. $^{13}$C nmr (100 MHz, $CDCl_3$) δ 40.9, NMe$_2$; 109.8, C6; 116.7, d ($^2J_{CF}$=22 Hz), C3; 120.3, d ($^3J_{CF}$=8 Hz), C4; 123.8, d ($^2J_{CF}$=8 Hz), C1; 147.4, C5; 157.6, d ($^1J_{CF}$=248 Hz), C2; 187.8, d ($^3J_{CF}$=7 Hz), CHO. MS (ESI+ve) m/z 168 (M+H, 100%). HRMS (ESI+ve) m/z 168.08192, $C_9H_{11}FNO$ requires 168.08192 (Δ=0.0 ppm).

c) Preparation of 2,5-difluoro-4-methylaminobenaldehyde (x)

Step 1: Preparation of 2,5-difluoro-4-methylaminobenzonitrile

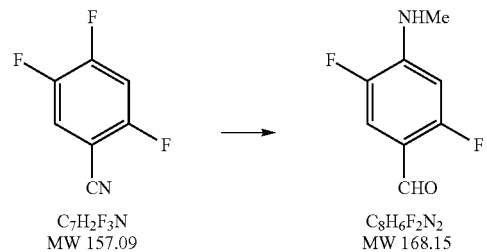 [SMILES: N#Cc1cc(F)c(F)cc1F ; CNc1cc(F)c(C=O)cc1F]

C$_7$H$_2$F$_3$N
MW 157.09

C$_8$H$_6$F$_2$N$_2$
MW 168.15

To a solution of 2,4,5-trifluorobenzonitrile (0.575 g, 3.7 mmol) in ethanol (20 ml) was added methylamine (30% aq, 4.2 ml, 37 mmol) and the mixture stirred for 3 h. The reaction mixture was then partitioned between diethyl ether (100 ml) and water (100 ml), and the aqueous layer re-extracted with diethyl ether (100 ml). The combined ether extract was washed with brine (200 ml), dried (MgSO$_4$) and evaporated to give 2,5-difluoro-4-methylaminobenzonitrile (0.549 g, 89%), mp 160-163° C.

$^1$H nmr (500 MHz, $CDCl_3$) δ 2.92, d (J=5.0 Hz), 3H, NMe; 4.68, br, 1H, NH; 6.36, dd (J=7.3, 10.8 Hz), 1H, H3; 7.10, dd (J=6.0, 11.0 Hz), 1H, H6. MS (ESI+ve) m/z 169 (MH$^+$, 100%).

Step 2: Preparation of 2,5-difluoro-4-methylaminobenzaldehyde (x)

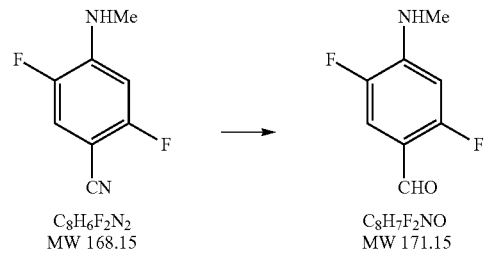 [SMILES: CNc1cc(F)c(C#N)cc1F ; CNc1cc(F)c(C=O)cc1F]

C$_8$H$_6$F$_2$N$_2$
MW 168.15

C$_8$H$_7$F$_2$NO
MW 171.15

To a solution of 2,5-difluoro-4-methylaminobenzonitrile (0.509 g, 3.03 mmol) in dry diethyl ether (40 ml) stirred at room temperature under nitrogen, was added dropwise by syringe diisobutylaluminium hydride (5.5 ml, 1.0 M in toluene, 5.5 mmol) and stirring continued for 16 h. The solution was chilled in an ice-bath and methanol (2.8 ml) was added dropwise and the mixture stirred for 1 h before 1.0 M HCl (17 ml) was added and stirring continued for a further 1 h. The reaction mixture was then partitioned between ether (50 ml) and water (50 ml) and the aqueous layer re-extracted with ether (50 ml). The combined ether extract was washed with 5% sodium bicarbonate solution (34 ml), then brine, dried (MgSO$_4$) and evaporated to give a mixture of the desired aldehyde and unhydrolysed imine (0.511 g). The material was filtered through a plug of silica gel using 100% dichloromethane to give pure 2,5-difluoro-4-methylaminobenzaldehyde (x).

(0.481 g, 94%), mp 133-138° C.

$^1$H nmr (400 MHz, CDCl$_3$) δ 2.95, s, 3H, NMe; 4.79, br, 1H, NH; 6.30, dd (J=6.8, 12.0 Hz), 1H, H3; 7.41, dd (J=6.0, 11.6 Hz), 1H, H6; 10.07, d (J=3.2 Hz), 1H, CHO. $^{13}$C nmr (100 MHz, d$_6$-dmso) δ 29.2, NHMe; 96.8, dd ($^2J_{CF}$=28 Hz, $^3J_{CF}$=4 Hz), C3; 110.0, dd ($^2J_{CF}$=11 Hz, $^3J_{CF}$=5 Hz), C1; 111.5, dd ($^2J_{CF}$=28 Hz, $^3J_{CF}$=5 Hz), C6; 145.3, app t ($^{2/3}J_{CF}$=14 Hz), C4; 146.8, d ($^1J_{CF}$=237 Hz), C5; 162.9, d ($^1J_{CF}$=250 Hz), C2; 183.9, d ($^3J_{CF}$=5 Hz), CHO. MS (ESI+ve) m/z 194 (MNa$^+$, 100%), 172 (MH$^+$, 30). HRMS (ESI+ve) m/z 194.03877, C$_8$H$_7$F$_2$NONa requires 194.03879 (Δ=0.1 ppm).

Example 12

Clonogenic Survival Cell Culture Assay for Cytotoxicity and Radioprotective Activity The assay involves the transformed human keratinocyte cell line (FEP 1811) (as described by Smith et al (6)) and evaluation of cytotoxicity and radioprotective activity using the clonogenic survival endpoint. The details are described in detail in Martin et al (4) (the disclosure of which is included herein in its entirety by way of reference), but briefly, mid-log phase monolayer cultures are incubated with various concentrations of the test drugs for one hour, after which the monolayers are washed and dispersed into single cell suspensions using pronase, and finally appropriate numbers of cells are dispensed into Petri dishes. Colonies are counted after eight days incubation. For radioprotection studies, the monolayer cultures are irradiated in a $^{137}$Cs-Gamma-cell radiation source to a dose of 12 Gy. The irradiation (with a dose rate of 0.6 Gy per minute) is started 30 minutes after addition of the test drug. After completion of irradiation, incubation of cultures is continued until the total time of exposure to the drug reaches 60 minutes. Cultures are then washed and plated for clonogenic survival as described for the cytotoxicity experiments. The experiments include untreated cultures as controls, and the plating efficiency of these controls is used to adjust that of the test cultures, in order to calculate the overall clonogenic survival.

In general each experiment involves investigation of 4 or 5 different test concentrations of the drug under study, with and without irradiation. The data analysis for the experiments with un-irradiated cells generates curves showing the relationship between cell survival and drug concentration (FIG. 1), from which the drug concentration corresponding to 50% survival (C$_{50}$) is determined. The results shown in FIG. 1 demonstrate the decreased cytotoxicity of compounds of the invention compared to the known radioprotector compound methylproamine (as described by Martin et al (4)).

Figure 2:
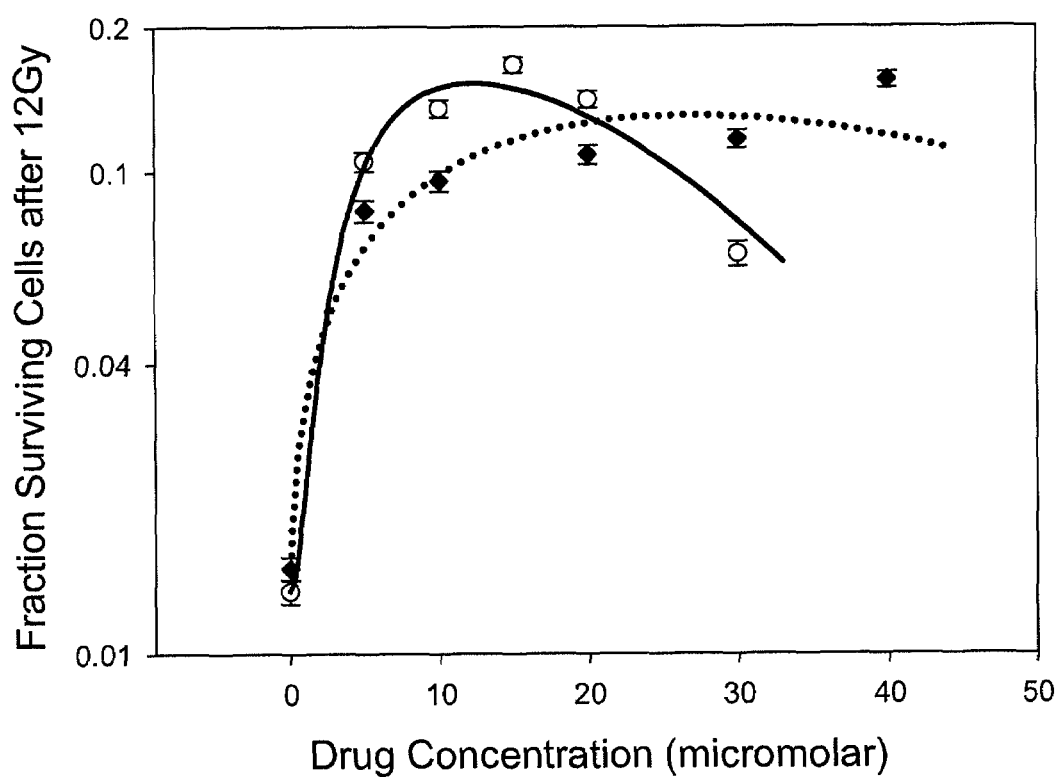
FIG. 2 shows a plot of clonogenic survival of cells exposed to a radiation dose of 12 Gy against various radioprotector concentrations (μM). The data for methylproamine (Formula I; X=MeN, Y=N, Z=N, $R_1$=Me, $R_3$=$NMe_2$) is represented by open circles and the solid line. The filled diamonds and dotted line show the data for the compound of Example 1 (orthoFluoroProamine) (Formula I; X=MeN, Y=N, Z=N, $R_1$=F, $R_3$=$NMe_2$).

For irradiated cells, increasing concentrations of the compounds of the invention first increases clonogenic survival, demonstrating the radioprotective effect. However, for some of the compounds, the survival decreases at higher drug concentrations, due to cytotoxicity. Non-linear regression analysis of the data, for example that in FIG. 2, generates a parameter denoted the protection factor (PF), which is the ratio of the maximum survival to the radiation-only (zero drug) survival. PF is therefore a measure of radioprotective efficacy. The C$_{50}$ and PF values, and for a number of the compounds are collected in Table 1, with standard deviations (SD) for those compounds that have been studied in replicate experiments.

TABLE 1

Clonogenic survival assay results for cytotoxicity and radioprotection

| | | | | phe ring substituents | | | | | Clonogenic survival data | | | |
| | | | | R1 | R2 | R3 | R4 | R5 | # | cytotoxicity | | radioprotection |
| Drug | X | Y | Z | (o) | (m) | (p) | (m) | (o) | exps | C50 | C50 sd | PF | PF sd |
|---|---|---|---|---|---|---|---|---|---|---|---|---|---|
| Known radioprotector (methylproamine) | MeN | N | N | Me | — | NMe$_2$ | — | — | 5 | 19.3 | 3.3 | 10 | 4.6 |
| Example 1 compound (orthoFluoroProamine) | MeN | N | N | F | — | NMe$_2$ | — | — | 4 | 28 | 10 | 9.3 | 1.4 |
| Example 2 compound (2,6 di-Fluoro Para-N-diMethylAmino Hoechst) | MeN | N | N | F | — | NMe$_2$ | — | F | 1 | 25 | | 6.4 | |
| Example 3 compound (OFPM) | MeN | N | N | F | — | NHMe | — | — | 3 | 218 | 63 | 7 | 2.4 |
| Example 4 compound (orthochloroproamine) | MeN | N | N | Cl | — | NMe$_2$ | — | — | 1 | 18 | | 5.5 | |
| Example 5 compound (OMe-mFHoechst) | MeN | N | N | — | F | OMe | — | — | 1 | 91 | | 2.1 | |
| Example 6 compound (paraFluoroHoechst) | MeN | N | N | — | — | F | — | — | 1 | 34 | | 4.5 | |
| Example 7 compound (metaFluoroProamine) | MeN | N | N | — | — | F | NMe$_2$ | — | 1 | 26 | | 3.2 | |
| Example 8 compound (OFMPM) | MeN | N | N | F | — | — | NHMe | — | 2 | 151 | 3.5 | 15.5 | 0.07 |
| Example 9 compound (OFMP) | MeN | N | N | F | — | — | NME$_2$ | — | 2 | 21.9 | 4.4 | 16.7 | 0.57 |
| Example 10 compound (DFPM) | MeN | N | N | F | — | NHMe | F | — | 2 | 51.4 | 4.1 | 9.62 | 2.18 |

REFERENCES

1. Waselenko, J. K., MacVittie, T. J., Blakely, W. F., Pesik, N., Wiley, A. L., Dickerson, W. E., Tsu, H., Confer, D. L., Coleman, C. N., Seed, T., Lowry, P., Armitage, J. O., and Dainiak, N. Medical management of the acute radiation syndrome: recommendations of the Strategic National Stockpile Radiation Working Group. *Ann Intern Med,* 140: 1037-1051, 2004.
2. Smith, P. J. and Anderson, C. O., *Int. J. Radiat. Biol.,* 46, 331 (1984).
3. Young, S. D. and Hill, R. P., *Brit. J. Cancer,* 60, 715-721 (1989).
4. Martin R F, Broadhurst S, Reum M E, Squire C J, Clark G R, Lobachevsky P N, White J M, Clark C, Sy D, Spotheim-Maurizot M, Kelly D P. In vitro studies with methylproamine: a potent new radioprotector. *Cancer Res.* 64(3):1067-70 (2004)
5. Kelly, D. P.; Bateman, S. A.; Hook, R. J.; Martin, R. F.; Reum, M. E.; Rose, M.; Whittaker, A. R. D. *Aust. J. Chem.* 1994, 47, 1751-1769

6. Smith P P, Bryant E M, Kaur P, McDougall J K, Cytogenetic analysis of eight human papillomavirus immortalized human keratinocyte cell lines, *Int. J. Cancer,* 1989 Dec. 15; 44(6):1124-31.

The invention claimed is:

1. A radioprotector compound of formula (I)

Formula (I)

wherein:
X is alkylamino;
Y and Z are N;
$R_3$ is $N(R)_2$ or NHR, where R is $C_1$ to $C_4$ alkyl;
$R_1$, $R_2$, $R_4$ and $R_5$ are selected from fluorine and hydrogen and at least one of $R_1$, $R_2$, $R_4$ and $R_5$ is F; and
$R_6$ to $R_{11}$ are hydrogen.

2. A radioprotector compound of formula (I)

Formula (I)

wherein:
X is alkylamino;
Y and Z are N;
$R_2$ is $N(R)_2$ or NHR, where R is $C_1$ to $C_4$ alkyl;
$R_1$, $R_3$, $R_4$ and $R_5$ are selected from fluorine and hydrogen and at least one of $R_1$, $R_3$, $R_4$ and $R_5$ is F; and
$R_6$ to $R_{11}$ are hydrogen.

3. A radioprotector compound of formula (I)

Formula (I)

wherein:
X is alkylamino;
Y and Z are N;
$R_3$ is $N(R)_2$ or NHR, where R is $C_1$ to $C_4$ alkyl;
$R_1$ is fluorine; and
$R_2$ and $R_4$ to $R_{11}$ are hydrogen.

4. A radioprotector compound which is selected from:

5. A pharmaceutical composition comprising a compound of claim 1 and one or more pharmaceutically acceptable carriers and/or diluents.

6. A method of cancer radiotherapy which comprises preferentially administering to non-tumour cells and tissues in a subject in need of such therapy an amount of a compound of claim 3 effective to minimise damage to the non-tumour cells and tissues, and subjecting the locus of a tumour in the subject to radiation.

7. A pharmaceutical composition comprising a compound of claim 3 and one or more pharmaceutically acceptable carriers and/or diluents.

8. A method of cancer radiotherapy which comprises preferentially administering to non-tumour cells and tissues in a subject in need of such therapy an amount of a compound of claim 4 effective to minimise damage to the non-tumour cells and tissues, and subjecting the locus of a tumour in the subject to radiation.

9. A pharmaceutical composition comprising a compound of claim 4 and one or more pharmaceutically acceptable carriers and/or diluents.

\* \* \* \* \*